(12) United States Patent
Moleda

(10) Patent No.: US 12,343,515 B2
(45) Date of Patent: *Jul. 1, 2025

(54) NEEDLE-BASED DEVICE WITH A SAFETY MECHANISM IMPLEMENTED THEREIN

(71) Applicant: Jaroslaw Moleda, Warsaw (PL)

(72) Inventor: Jaroslaw Moleda, Warsaw (PL)

(73) Assignee: MediVena Sp. z o.o., Warsaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,330

(22) Filed: Sep. 7, 2023

(65) Prior Publication Data

US 2023/0414881 A1 Dec. 28, 2023

Related U.S. Application Data

(63) Continuation of application No. 18/223,294, filed on Jul. 18, 2023, now Pat. No. 11,890,459, which is a
(Continued)

(51) Int. Cl.
*A61M 5/32* (2006.01)
*A61M 5/31* (2006.01)
(Continued)

(52) U.S. Cl.
CPC ........ *A61M 5/3202* (2013.01); *A61M 5/3129* (2013.01); *A61M 5/3148* (2013.01);
(Continued)

(58) Field of Classification Search
CPC .............. A61M 5/3202; A61M 5/3129; A61M 5/3148; A61M 5/31571; A61M 5/3243;
(Continued)

(56) References Cited

U.S. PATENT DOCUMENTS 3,865,236 A 2/1975 Rycroft
4,425,120 A 1/1984 Sampson et al.
(Continued)

FOREIGN PATENT DOCUMENTS

CN 111888580 B 3/2022
EP 1317938 B1 7/2006
(Continued)

OTHER PUBLICATIONS

"Insulin Safety Syringes", by Medivena, Found Online on [May 31, 2021] https://www.one-care.com/safety-insulin-syringes.
(Continued)

*Primary Examiner* — James D Ponton
*Assistant Examiner* — Hong-Van N Trinh
(74) *Attorney, Agent, or Firm* — LEGALFORCE RAPC WORLDWIDE

(57) ABSTRACT

A needle-based device includes a body, a needle protruding from the body for a length thereof, and a needle shield encompassing an entirety of the protruding length of the needle to protect the needle in a first state of disuse of the needle-based device. The needle shield is retracted in a direction toward the body to apply a force in the direction to cause the needle to emerge out of the needle shield to prepare the needle-based device for a second state of use thereof. The needle-based device also includes a lock button including a hook at an end thereof. The needle shield is locked using the lock button in the first state of disuse in accordance with the hook passing through a groove formed on the needle shield and locking directly on to a top of the body from which the needle protrudes.

20 Claims, 18 Drawing Sheets

Related U.S. Application Data continuation-in-part of application No. 18/221,848, filed on Jul. 13, 2023, now Pat. No. 12,005,244, application No. 18/243,330 is a continuation of application No. 18/221,848, filed on Jul. 13, 2023, now Pat. No. 12,005,244, application No. 18/243,330 is a continuation of application No. 17/494,904, filed on Oct. 6, 2021, now Pat. No. 11,786,672, said application No. 18/221,848 is a continuation-in-part of application No. 17/494,904, filed on Oct. 6, 2021, now Pat. No. 11,786,672, which is a continuation of application No. 17/234,793, filed on Apr. 19, 2021, now Pat. No. 11,224,699, and a continuation of application No. 16/831,824, filed on Mar. 27, 2020, now Pat. No. 11,173,254, said application No. 17/234,793 is a continuation-in-part of application No. 16/831,824, filed on Mar. 27, 2020, now Pat. No. 11,173,254.

(51) Int. Cl.
  *A61M 5/315* (2006.01)
  *A61M 5/20* (2006.01)

(52) U.S. Cl.
  CPC ...... *A61M 5/31571* (2013.01); *A61M 5/3234* (2013.01); *A61M 5/3243* (2013.01); *A61M 5/3257* (2013.01); *A61M 5/326* (2013.01); *A61M 5/3271* (2013.01); *A61M 2005/2073* (2013.01)

(58) Field of Classification Search
  CPC .. A61M 5/3234; A61M 5/3257; A61M 5/326; A61M 5/3271; A61M 5/31566; A61M 5/3205; A61M 5/321; A61M 5/3216; A61M 5/3213; A61M 5/3245; A61M 5/3269; A61M 5/3272; A61M 5/3273; A61M 5/3275; A61M 5/3219; A61M 2005/2073; A61M 2005/3247; A61M 2005/3267; A61M 2005/3217; A61M 2005/3246; A61M 2005/3249; A61M 2005/325; A61M 2005/3252; A61M 2005/3253; A61M 2005/3254; A61M 2005/3256; A61M 2005/3258; A61M 2005/3261; A61M 2005/3263; A61M 2005/3264; A61M 2005/3268; A61M 2005/3265
  See application file for complete search history.

(56) References Cited

U.S. PATENT DOCUMENTS

| | | | |
|---|---|---|---|
| 4,631,057 A | 12/1986 | Mitchell | |
| 4,636,201 A | 1/1987 | Ambrose et al. | |
| 4,654,034 A | 3/1987 | Masters et al. | |
| 4,735,617 A | 4/1988 | Nelson et al. | |
| 4,752,290 A | 6/1988 | Schramm | |
| 4,795,432 A | 1/1989 | Karczmer | |
| 4,810,248 A | 3/1989 | Masters et al. | |
| 4,826,488 A | 5/1989 | Nelson et al. | |
| 4,850,994 A | 7/1989 | Zerbst et al. | |
| 4,894,055 A | 1/1990 | Sudnak | |
| 4,897,083 A | 1/1990 | Martell | |
| 4,900,311 A | 2/1990 | Stern et al. | |
| 4,911,693 A | 3/1990 | Paris | |
| 4,915,701 A * | 4/1990 | Halkyard | A61M 5/3271 604/232 |
| 4,927,019 A | 5/1990 | Haber | |
| 4,932,940 A | 6/1990 | Walker et al. | |
| 4,950,242 A | 8/1990 | Alvarez | |
| 4,950,250 A | 8/1990 | Haber et al. | |
| 4,964,866 A | 10/1990 | Szwarc | |
| 4,966,592 A | 10/1990 | Burns et al. | |
| 4,982,842 A | 1/1991 | Hollister | |
| 4,998,920 A | 3/1991 | Johnson | |
| 4,998,922 A | 3/1991 | Kuracina et al. | |
| 5,002,536 A | 3/1991 | Thompson et al. | |
| 5,041,099 A | 8/1991 | Gelabert | |
| 5,057,087 A | 10/1991 | Harmon | |
| 5,085,647 A | 2/1992 | Henderson et al. | |
| 5,104,385 A | 4/1992 | Huband | |
| 5,104,386 A | 4/1992 | Alzain | |
| 5,152,750 A | 10/1992 | Haining | |
| 5,163,917 A | 11/1992 | Huefner et al. | |
| 5,181,524 A | 1/1993 | Wanderer et al. | |
| 5,188,613 A | 2/1993 | Shaw | |
| 5,193,552 A | 3/1993 | Columbus et al. | |
| 5,207,646 A | 5/1993 | Brunel | |
| 5,209,739 A | 5/1993 | Talalay | |
| 5,215,534 A | 6/1993 | De Harde et al. | |
| 5,222,945 A | 6/1993 | Basnight | |
| 5,246,427 A | 9/1993 | Sturman et al. | |
| 5,254,099 A | 10/1993 | Kuracina et al. | |
| 5,256,153 A | 10/1993 | Hake | |
| 5,259,841 A | 11/1993 | Hohendorf et al. | |
| 5,267,961 A | 12/1993 | Shaw | |
| 5,269,761 A | 12/1993 | Stehrenberger et al. | |
| 5,312,347 A | 5/1994 | Osborne et al. | |
| 5,342,323 A | 8/1994 | Haining | |
| 5,366,447 A | 11/1994 | Gurley | |
| 5,368,577 A | 11/1994 | Teoh et al. | |
| 5,385,557 A | 1/1995 | Thompson | |
| 5,401,246 A | 3/1995 | Mazur et al. | |
| 5,403,288 A | 4/1995 | Stanners | |
| 5,411,487 A | 5/1995 | Castagna | |
| 5,498,244 A | 3/1996 | Eck | |
| 5,562,625 A | 10/1996 | Stefancin, Jr. | |
| 5,582,594 A | 12/1996 | Chen | |
| 5,591,138 A | 1/1997 | Vaillancourt | |
| 5,595,566 A | 1/1997 | Vallelunga et al. | |
| 5,647,849 A | 7/1997 | Kalin | |
| 5,651,774 A | 7/1997 | Taranto et al. | |
| 5,658,259 A | 8/1997 | Pearson et al. | |
| 5,674,203 A | 10/1997 | Lewandowski | |
| 5,688,241 A | 11/1997 | Asbaghi | |
| 5,879,337 A | 3/1999 | Kuracina et al. | |
| 5,997,513 A | 12/1999 | Smith et al. | |
| 6,004,296 A | 12/1999 | Jansen et al. | |
| 6,156,012 A | 12/2000 | Nathan | |
| 6,162,197 A * | 12/2000 | Mohammad | A61B 5/153 604/196 |
| 6,413,236 B1 | 7/2002 | Van Dyke | |
| 6,436,075 B1 | 8/2002 | Liao | |
| 6,537,257 B1 | 3/2003 | Wien | |
| 6,692,470 B2 | 2/2004 | Sanpietro | |
| 6,752,788 B2 | 6/2004 | Tuen | |
| 6,776,775 B1 | 8/2004 | Mohammad | |
| 6,817,989 B2 | 11/2004 | Svendsen et al. | |
| 6,926,697 B2 | 8/2005 | Malenchek | |
| 7,041,092 B2 | 5/2006 | Barrelle | |
| 7,282,042 B2 | 10/2007 | Wang | |
| 7,300,420 B2 | 11/2007 | Doyle | |
| 7,314,464 B2 | 1/2008 | Giambattista et al. | |
| 7,329,238 B2 | 2/2008 | Halseth et al. | |
| 7,381,199 B2 | 6/2008 | Kuan | |
| 7,455,661 B2 | 11/2008 | Barrelle et al. | |
| 7,462,168 B2 | 12/2008 | Stonehouse et al. | |
| 7,462,169 B2 | 12/2008 | Follman et al. | |
| 7,497,847 B2 | 3/2009 | Crawford et al. | |
| 7,666,164 B2 | 2/2010 | Giambattista et al. | |
| 7,727,190 B2 | 6/2010 | Miller | |
| 7,799,002 B2 | 9/2010 | Dillard, III | |
| 7,922,698 B2 | 4/2011 | Riesenberger et al. | |
| 8,226,630 B2 | 7/2012 | Ackerman | |
| 8,337,468 B1 | 12/2012 | Reis et al. | |
| 8,545,454 B2 | 10/2013 | Kuracina et al. | |
| 8,617,119 B2 | 12/2013 | Liversidge | |
| 8,715,231 B2 | 5/2014 | Woehr | |
| 8,747,355 B2 | 6/2014 | Rubinstein et al. | |
| 9,022,979 B2 | 5/2015 | Woehr | |
| 9,248,242 B2 | 2/2016 | Verespej et al. | |

(56) References Cited

U.S. PATENT DOCUMENTS

| | | |
|---|---|---|
| 9,248,244 B2 | 2/2016 | Roberts et al. |
| 9,327,086 B2 | 5/2016 | Tsals et al. |
| 9,352,099 B2 | 5/2016 | Roberts et al. |
| 9,421,336 B2 | 8/2016 | Ekman et al. |
| 9,440,032 B2 | 9/2016 | Roberts et al. |
| 9,586,011 B2 | 3/2017 | Roberts et al. |
| 9,649,452 B2 | 5/2017 | Srinivasan et al. |
| 9,750,894 B2 | 9/2017 | Quinn et al. |
| 9,789,264 B2 | 10/2017 | Roberts et al. |
| 9,913,750 B2 | 3/2018 | Lerner |
| 9,931,476 B2 | 4/2018 | Zhang et al. |
| 10,159,808 B2 | 12/2018 | Samandi et al. |
| 10,166,334 B2 | 1/2019 | Wyrick |
| 10,220,157 B2 | 3/2019 | Nguyen |
| 10,335,555 B2 | 7/2019 | Klippenstein |
| 10,398,858 B2 | 9/2019 | Newman et al. |
| 10,441,728 B2 | 10/2019 | Schader et al. |
| 10,518,042 B2 | 12/2019 | Keim et al. |
| 10,576,219 B2 | 3/2020 | Park |
| 10,661,026 B2 | 5/2020 | Smith et al. |
| 10,792,439 B2 | 10/2020 | Sanders et al. |
| 10,881,810 B2 | 1/2021 | Halm |
| 11,147,923 B2 | 10/2021 | Helmer |
| 11,173,254 B2 | 11/2021 | Moleda |
| 11,191,907 B2 | 12/2021 | Nober et al. |
| 11,202,861 B2 | 12/2021 | Wendland et al. |
| 11,224,699 B2 | 1/2022 | Moleda |
| 11,534,557 B2 | 12/2022 | Roberts et al. |
| 11,786,672 B2* | 10/2023 | Moleda ............... A61M 5/326 604/198 |
| 11,890,459 B2* | 2/2024 | Moleda ............... A61M 5/3148 |
| 2003/0055383 A1 | 3/2003 | Bush et al. |
| 2003/0187401 A1 | 10/2003 | Doyle |
| 2004/0030294 A1 | 2/2004 | Mahurkar |
| 2005/0119627 A1 | 6/2005 | Crawford |
| 2005/0171486 A1 | 8/2005 | Hochman |
| 2005/0203466 A1 | 9/2005 | Hommann et al. |
| 2005/0240160 A1 | 10/2005 | Lin |
| 2005/0277892 A1 | 12/2005 | Chen |
| 2006/0100589 A1 | 5/2006 | Lin |
| 2006/0173409 A1 | 8/2006 | Yang |
| 2006/0282044 A1 | 12/2006 | Mohammed |
| 2007/0073224 A1 | 3/2007 | Dries |
| 2007/0078409 A1 | 4/2007 | Saltz |
| 2008/0177238 A1 | 7/2008 | Follman et al. |
| 2009/0157010 A1 | 6/2009 | Martin |
| 2012/0022463 A1 | 1/2012 | Wu |
| 2013/0079715 A1 | 3/2013 | Wu |
| 2013/0261559 A1 | 10/2013 | Werbickas |
| 2013/0261564 A1 | 10/2013 | Wong |
| 2014/0039406 A1 | 2/2014 | Verespej et al. |
| 2014/0088513 A1 | 3/2014 | Darichuk et al. |
| 2015/0038922 A1 | 2/2015 | Slemmen et al. |
| 2015/0133870 A1 | 5/2015 | Ashworth et al. |
| 2015/0272492 A1 | 10/2015 | Schraga |
| 2016/0354550 A1 | 12/2016 | Ward et al. |
| 2017/0182260 A1 | 6/2017 | Schraga |
| 2018/0161520 A1 | 6/2018 | Smith et al. |
| 2018/0200487 A1 | 7/2018 | Sokolski et al. |
| 2018/0243514 A1 | 8/2018 | Kim et al. |
| 2019/0030293 A1 | 1/2019 | Rogers et al. |
| 2019/0151564 A1 | 5/2019 | Schrul et al. |
| 2019/0151565 A1 | 5/2019 | Groetzbach et al. |
| 2019/0374717 A1 | 12/2019 | Swanson et al. |
| 2021/0299361 A1 | 9/2021 | Moleda |
| 2021/0299364 A1 | 9/2021 | Moleda |
| 2021/0369976 A1 | 12/2021 | Chevallier |
| 2023/0201483 A1 | 6/2023 | Sanders et al. |
| 2024/0123157 A1* | 4/2024 | Moleda ............... A61M 5/3148 |
| 2024/0139423 A1* | 5/2024 | Moleda ............... A61M 5/3243 |

FOREIGN PATENT DOCUMENTS

| | | |
|---|---|---|
| EP | 1949929 B1 | 11/2009 |
| EP | 3360592 A1 | 8/2018 |
| EP | 3017838 B1 | 5/2019 |
| EP | 2883563 B1 | 3/2021 |
| KR | 200191613 Y1 | 8/2000 |
| KR | 20190128609 A | 11/2019 |
| WO | 1990014112 A1 | 11/1990 |
| WO | 9220390 A1 | 11/1992 |
| WO | 1994004205 A1 | 3/1994 |
| WO | 1997027891 A1 | 8/1997 |
| WO | 2001045776 A1 | 6/2001 |
| WO | 2003015855 A1 | 2/2003 |
| WO | 2003066141 A1 | 8/2003 |
| WO | 2003082385 A1 | 10/2003 |
| WO | 2004060445 A2 | 7/2004 |
| WO | 2007077463 A1 | 7/2007 |
| WO | 2008127195 A1 | 10/2008 |
| WO | 2008146033 A1 | 12/2008 |
| WO | 2011107954 A2 | 9/2011 |
| WO | 2011162913 A1 | 12/2011 |
| WO | 2012000834 A1 | 1/2012 |
| WO | 2012000835 A1 | 1/2012 |
| WO | 2012093073 A1 | 7/2012 |
| WO | 2013064475 A1 | 5/2013 |
| WO | 2017179813 A1 | 10/2017 |
| WO | 2018111797 A2 | 6/2018 |
| WO | 2019010689 A1 | 1/2019 |
| WO | 2021191670 A1 | 9/2021 |
| WO | 2023057959 A1 | 4/2023 |

OTHER PUBLICATIONS

"ONE_CARE Insulin Safety Syringes", by Medivena, Found Online on [May 31, 2021] https://static1.squarespace.com/static/5c2e33d43917eeb9b98da746/1/5e85017fc8068858c09e1e44/158577498210/ONE-CARE%E2%84%A2+Insulin+Safety+Syringes+_+website.pdf.

"Single Use Safety Syringe With Passive Needlestick Injury & Reuse Prevention" By Alfa Corpuscles Pvt. Ltd., Found Online On [May 31, 2021] https://birac.nic.in/product-detail.php?product=56.

"Ritract safety syringe", by BerryDesign, Published online in [2005] https://www.berrydesign.com.au/portfolios/medical/ritract-safety-syringe.php.

"An introduction to needlestick protection and safety syringes", by Springboard, Published Online on [Jun. 13, 2018] https://www.springboard.pro/safety-syringes/.

"Use of safety-engineered devices by healthcare workers for intravenous and/or phlebotomy procedures in healthcare settings: a systematic review and meta-analysis", by Rami A. Ballout et al., Published at BMC Health Services Research, Found Online [Oct. 5, 2023] https://bmchealthservres.biomedcentral.com/counter/pdf/10.1186/s12913-016-1705-y.pdf.

"Developing safe porter protective syringe cap to prevent percutaneous injuries; a semi-experimental study", by Zeynep Akidagi et al., Published at International Journal Of Community Medicine And Public Health vol. 9 No. 5, Published on [May 27, 2022] https://www.ijcmph.com/index.php/ijcmph/article/view/9647/5911.

"Devices for preventing percutaneous exposure injuries caused by needles in healthcare personnel",by Marie-Claude Lavoie et al., Published at Cochrane Library, Published on [Mar. 9, 2014] https://www.cochranelibrary.com/cdsr/doi/10.1002/14651858.CD009740.pub2/full.

"Safe and effective use of a passive safety needle by healthcare professionals in a simulated environment, including perceptions and preferences", by Anna Serafin et al., Published at Taylor & Francis, Published on [Sep. 11, 2023] https://www.tandfonline.com/doi/epdf/10.1080/17434440.2023.2254680?needAccess=true.

"Needle Stick Injuries: An Overview of the Size of the Problem, Prevention & Management", by Moazzam A. Zaidi et al, Published at Ibnosina Journal of Medicine and Biomedical Sciences, Published on [Mar. 1, 2010] https://www.thieme-connect.com/products/ejournals/pdf/10.4103/1947-489X.210971.pdf.

(56) References Cited

OTHER PUBLICATIONS

"Role of Safety-Engineered Devices in Preventing Needlestick Injuries in 32 French Hospitals", by F. Lamontagne et al., Published by The University of Chicago Press, Found Online [Oct. 5, 2023] https://sci-hub.hkvisa.net/10.1086/510814.

"Human Factors Analysis of Needle Safety Devices", by William A. Hyman, Published at Journal of Clinical Engineering, Found Online [Oct. 5, 2023] https://d2ghdaxqb194v2.cloudfront.net/577/165817.pdf.

"Evaluation Of A Safety Resheathable Winged Steel Needle For Prevention Of Percutaneous Injuries Associated With Intravascular-Access Procedures Among Healthcare Workers", by Meryl H. Mendelson, Published by The University of Chicago Press, Published on [Jan. 2, 2015] https://sci-hub.hkvisa.net/10.1086/502174.

* cited by examiner

NEEDLE-BASED DEVICE WITH A SAFETY MECHANISM IMPLEMENTED THEREIN

CLAIM OF PRIORITY

This Application is a Continuation Application of, and claims priority to, co-pending U.S. patent application Ser. No. 17/494,904 titled NEEDLE-BASED DEVICE WITH A SAFETY MECHANISM IMPLEMENTED THEREIN filed on Oct. 6, 2021, co-pending U.S. patent application Ser. No. 18/223,294 titled NEEDLE-BASED DEVICE WITH EXTERNAL SAFETY CAP AND A NEEDLE GUIDE ELEMENT THEREOF filed on Jul. 18 2023, and U.S. patent application Ser. No. 18/221,848 titled NEEDLE-BASED DEVICE BASED ON DIRECT WING-BASED COUPLING OF A NEEDLE SHIELD TO A BARREL THEREOF AND SAFETY MECHANISM IMPLEMENTED THEREIN filed on Jul. 13, 2023. Each of U.S. patent application Ser. No. 18/223,294 and U.S. patent application Ser. No. 18/221,848 claims priority to U.S. patent application Ser. No. 17/494,904, which is a U.S. Continuation Application of U.S. patent application Ser. No. 16/831,824 titled NEEDLE-BASED DEVICE WITH A SAFETY MECHANISM IMPLEMENTED THEREIN filed on Mar. 27, 2020 and issued on Nov. 16, 2021 as U.S. Pat. No. 11,173,254, and U.S. patent application Ser. No. 17/234,793 also titled NEEDLE-BASED DEVICE WITH A SAFETY MECHANISM IMPLEMENTED THEREIN" filed on Apr. 19, 2021 and issued as U.S. Pat. No. 11,224,699 on Jan. 18, 2022. U.S. patent application Ser. No. 17/234,793 is a Continuation-in-Part Application of and claims priority to U.S. patent application Ser. No. 16/831,824. The contents of each of the aforementioned applications are incorporated in entirety thereof in this Application by reference.

FIELD OF TECHNOLOGY

This disclosure relates generally to needle-based devices and, more particularly, to a needle-based device with a safety mechanism implemented therein.

BACKGROUND

A needle-based device may be a syringe, a hypodermic needle, a pen injector and/or a fluid collection device. Following a use of a needle thereof to inject a fluid (e.g., a medication) into a body of a patient or to extract another fluid therefrom, the needle may be covered with a cap for storage purposes. The needle may also be covered with the cap prior to the use thereof. Covering the needle with the cap and/or removing the cap of the needle may result in injuries to a user of the needle-based device. Some implementations of the needle-based device may employ a spring in a barrel of the needle-based device configured to enable retraction of the needle after use. However, a space in the barrel occupied by the spring may result in the needle-based device not capable of inserting the needle fully to a desired penetration depth and/or taking in a lesser quantity of a fluid compared to a spring-less implementation.

SUMMARY

Disclosed are methods, a device and/or a system of a needle-based device with a safety mechanism implemented therein.

In one aspect, a needle-based device includes a body, a needle protruding from the body for a length thereof, and a needle shield encompassing an entirety of the protruding length of the needle to protect the needle in a first state of disuse of the needle-based device. The needle shield is retracted in a first direction toward the body to apply a first force in the first direction to cause the needle to emerge out of the needle shield to prepare the needle-based device for a second state of use thereof. The needle-based device also includes a lock button with a first end either integrally formed with the needle shield or external to the needle shield and then coupled to the needle shield.

The lock button includes a hook at a second end thereof. A length of the lock button is completely external to the needle shield. The needle shield is locked using the lock button in the first state of disuse of the needle-based device in accordance with the hook of the lock button passing through a groove formed on the needle shield and locking directly on to a top of the body from which the needle protrudes such that, in the state of the locking of the needle shield, the length of the lock button completely external to the needle shield is parallel to a length of the needle shield and the entire protruding length of the needle, and the hook is perpendicular to the length of the needle shield, the length of the lock button and the entire protruding length of the needle.

In another aspect, a needle-based device includes a body, a needle protruding from the body for a length thereof, and a needle shield encompassing an entirety of the protruding length of the needle to protect the needle in a first state of disuse of the needle-based device. The needle shield is retracted in a first direction toward the body to apply a first force in the first direction to cause the needle to emerge out of the needle shield to prepare the needle-based device for a second state of use thereof. The needle-based device is transitioned back to the first state of disuse thereof following the second state of use in accordance with applying a second force in a second direction diametrically opposite to the first direction. The needle-based device also includes a lock button with a first end either integrally formed with the needle shield or external to the needle shield and then coupled to the needle shield.

The lock includes a hook at a second end thereof. A length of the lock button is completely external to the needle shield. The needle shield is locked using the lock button in the first state of disuse of the needle-based device in accordance with the hook of the lock button passing through a groove formed on the needle shield and locking directly on to a top of the body from which the needle protrudes such that, in the state of the locking of the needle shield, the length of the lock button completely external to the needle shield is parallel to a length of the needle shield and the entire protruding length of the needle, and the hook is perpendicular to the length of the needle shield, the length of the lock button and the entire protruding length of the needle.

In yet another aspect, a needle-based device includes a body, a needle protruding from the body for a length thereof, and a needle shield encompassing an entirety of the protruding length of the needle to protect the needle in a first state of disuse of the needle-based device. The needle shield is retracted in a first direction toward the body to apply a first force in the first direction to cause the needle to emerge out of the needle shield to prepare the needle-based device for a second state of use thereof. The needle-based device is transitioned back to the first state of disuse thereof following the second state of use in accordance with applying a second force in a second direction diametrically opposite to the first direction. The encompassing of the entire protruding length of the needle by the needle shield is securely maintained in the first state of disuse of the needle-based device through coupling between the needle shield and the body. The second state of use of the needle-based device encompasses drawing of a fluid and/or injection of the fluid via the needle-based device.

The needle-based device also includes a lock button with a first end either integrally formed with the needle shield or external to the needle shield and then coupled to the needle shield. The lock button includes a hook at a second end thereof. A length of the lock button is completely external to the needle shield. The needle shield is locked using the lock button in the first state of disuse of the needle-based device in accordance with the hook of the lock button passing through a groove formed on the needle shield and locking directly on to a top of the body from which the needle protrudes such that, in the state of the locking of the needle shield, the length of the lock button completely external to the needle shield is parallel to a length of the needle shield and the entire protruding length of the needle, and the hook is perpendicular to the length of the needle shield, the length of the lock button and the entire protruding length of the needle.

Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Example embodiments, as described below, may be used to provide methods, a system and/or a device of a needle-based device with a safety mechanism implemented therein. Although the present embodiments have been described with reference to specific example embodiments, it will be evident that various modifications and changes may be made to these embodiments without departing from the broader spirit and scope of the various embodiments.

Figure 1:
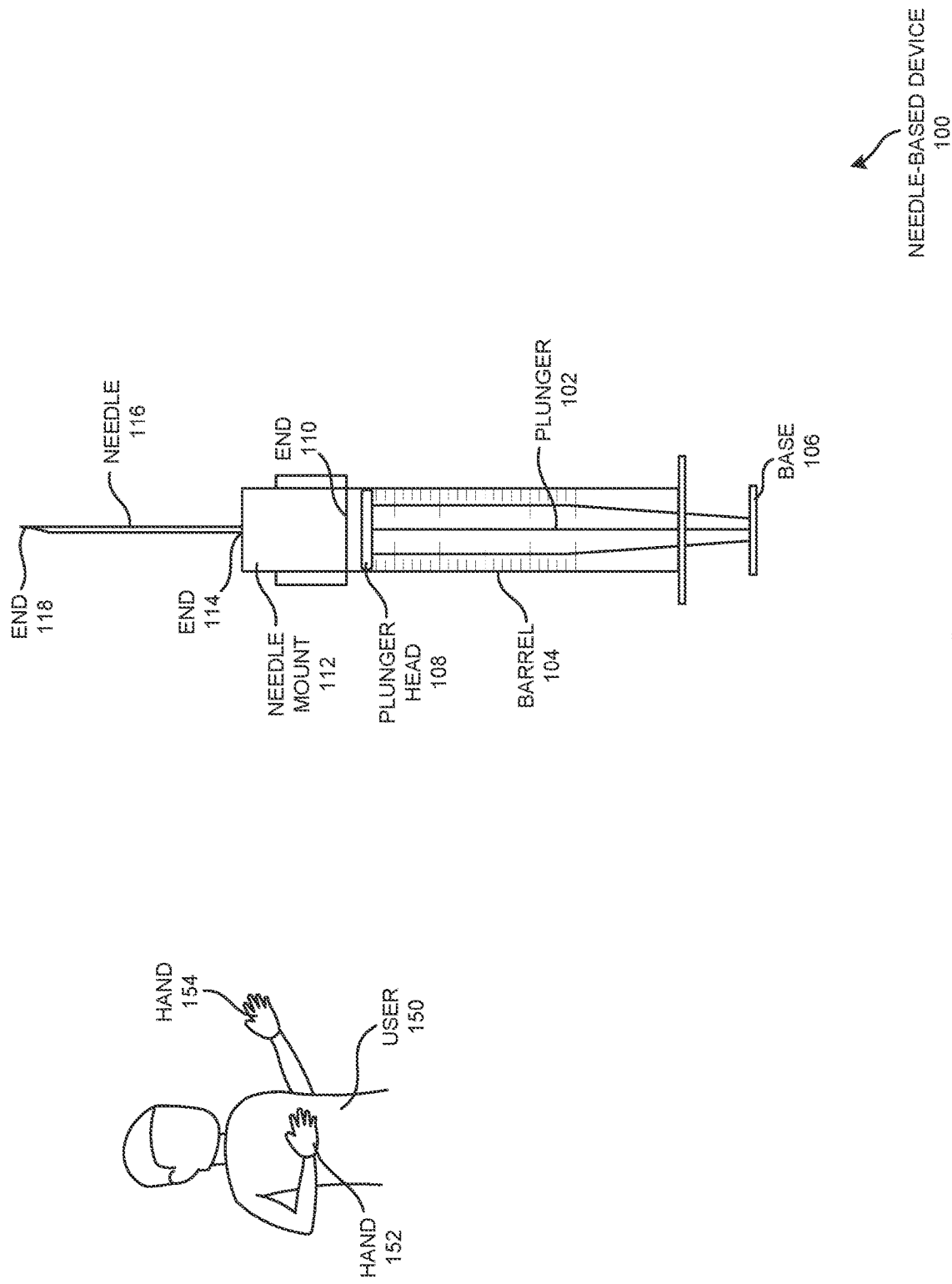
FIG. 1 is a schematic view of a needle-based device, according to one or more embodiments.

FIG. 1 shows a needle-based device 100, according to one or more embodiments. In one or more embodiments, needle-based device 100 may be a syringe, a hypodermic needle, a pen injector, a fluid (e.g., blood) collection device and/or a fluid injector/extractor. It should be noted that needle-based device 100 may not only be limited in use to medical applications but may also be used in biological applications and/or chemical applications. For example, needle-based device 100 may be used to extract a requisite quantity of a solvent/fluid from a vial/bottle. All reasonable applications are within the scope of the exemplary embodiments discussed herein.

In one or more embodiments, needle-based device 100 may include a plunger 102 configured to be moved in and out of a barrel 104 thereof. In one example implementation, barrel 104 may be cylindrical and plunger 102 may be appropriately designed (e.g., also cylindrical) to enable slidable movement thereof within barrel 104 and in and out of barrel 104. In another example implementation, barrel 104 may be shaped like a square prism or a rectangular prism and plunger 102 may be appropriately shaped to enable the aforementioned slidable movement. All possible shapes and configurations of barrel 104 and plunger 102 that enable the slidable movement of plunger 102 within barrel 104 and in and out of barrel 104 are within the scope of the exemplary embodiments discussed herein.

In one or more embodiments, a base 106 of plunger 102 may enable a user 150 to press plunger 102 into barrel 104 using a thumb of a hand 152 thereof; base 106 may also enable user 150 to draw plunger 102 out of barrel 104 using the thumb and/or other fingers of hand 152. In one or more embodiments, user 150 may be able to use the other fingers (e.g., forefinger and middle finger) and, optionally, a palm of hand 152 to stabilize needle-based device 100 while utilizing the thumb to press plunger 102 into barrel 104; user 150 may hold needle-based device 100 through another hand (e.g., hand 154) and draw plunger 102 out of barrel 104 using the thumb and/or the other fingers of hand 152. The use of plunger 102 and barrel 104 are well known to one skilled in the art with respect to needle-based devices; detailed discussion thereof is, therefore, skipped for the sake of convenience, brevity and clarity.

It should be noted that, in all states of operation of needle-based device 100, at least some portion of plunger 102 (e.g., at least base 106) may be outside barrel 104. It should also be noted that at least some portion of plunger 102 may be inside barrel 104 in all states of operation of needle-based device 100. For example, an end of plunger 102 farthest away from an end thereof including base 106 may be a plunger head 108. In one or more embodiments, plunger head 108 may be inside barrel 104 in all states of operation of needle-based device 100. In one or more embodiments, as shown in FIG. 1, a cross-sectional diameter of plunger head 108 may be less than a cross-sectional diameter of barrel 104, and a cross-sectional diameter of base 106 may be more than the cross-sectional diameter of barrel 104. The aforementioned designs are crucial to enable plunger 102 to move within barrel 104 to perform functionalities associated with needle-based device 100. Without base 106, it may not be possible for a position of plunger head 108 within barrel 104 to be desirably controlled. Without plunger head 108, plunger 102 may fall out of barrel 104 in a vertical position of needle-based device 100 with base 106 at a bottom thereof. Also, a portion of barrel 102 between plunger head 108 and an end 110 of barrel 104 farthest away from base 106 may include a fluid drawn from a vial/bottle by needle-based device 100. Said portion may not be able to hold the fluid without plunger head 108.

FIG. 1 also shows a needle mount 112, according to one or more embodiments. In one or more embodiments, an end 114 of a needle 116 may be inserted into needle mount 112 (e.g., a needle hub) such that needle 116 protrudes from needle mount 112. In one or more embodiments, needle 116 may include a hollow (e.g., cylindrical) bore along a length thereof. In one or more embodiments, another end 118 of needle 116 may be beveled into a point. In one or more embodiments, end 118 of needle 116 may be configured to first touch a vial/bottle during extraction of a fluid therefrom or an arm of a patient during injection of the fluid therein. In one or more embodiments, needle mount 112, in turn, may be directly coupled to barrel 104 by way of end 110 thereof farthest from base 106. Thus, in an implementation where barrel 104 and plunger 102 together may form a syringe, needle mount 112 and, thereby, needle 116 may be attached to the syringe.

Figure 2:
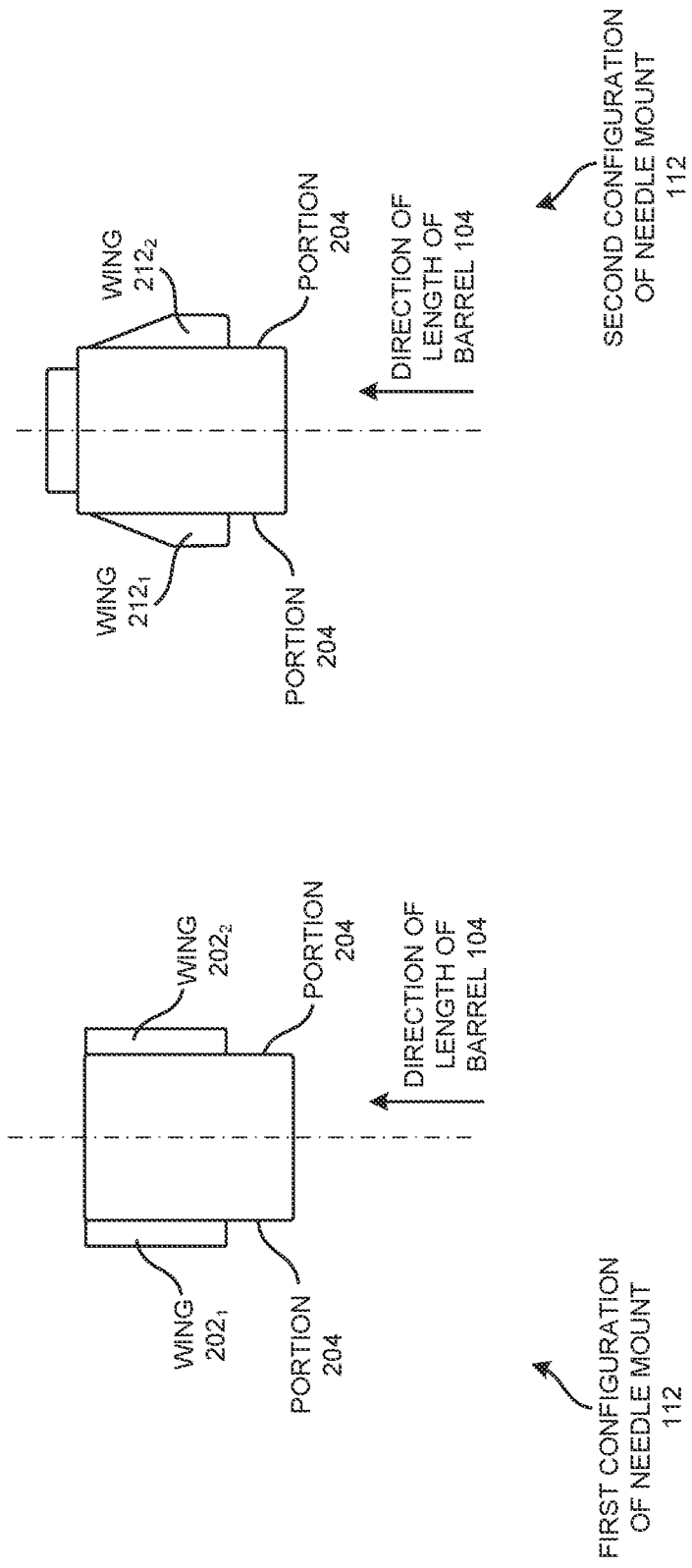
FIG. 2 is a schematic view of multiple configurations of a needle mount of the needle-based device of FIG. 1, according to one or more embodiments.

FIG. 2 shows multiple configurations of needle mount 112, according to one or more embodiments. In a first configuration, needle mount 112 may have a wing $202_{1,2}$ on each lateral side thereof in a direction approximately perpendicular to a length of barrel 104 when needle mount 112 is coupled to barrel 104. A portion 204 of needle mount 112 with no wings may be configured to be directly coupled (e.g., based on a screw mechanism) to barrel 104. In the first configuration, wings $202_{1-2}$ may be of uniform width. In a second configuration, again, needle mount 112 may have a wing $212_{1,2}$ on each lateral side thereof in the direction approximately perpendicular to the length of barrel 104 when needle mount 112 is coupled to barrel 104. Again, in the second configuration, a portion 214 of needle mount 112 with no wings may be configured to be directly coupled (e.g., based on a screw mechanism) to barrel 104. However, unlike the first configuration, wings $212_{1-2}$ may be only partially of uniform width, only to then taper off to a reduced width (or no width).

Figure 3:
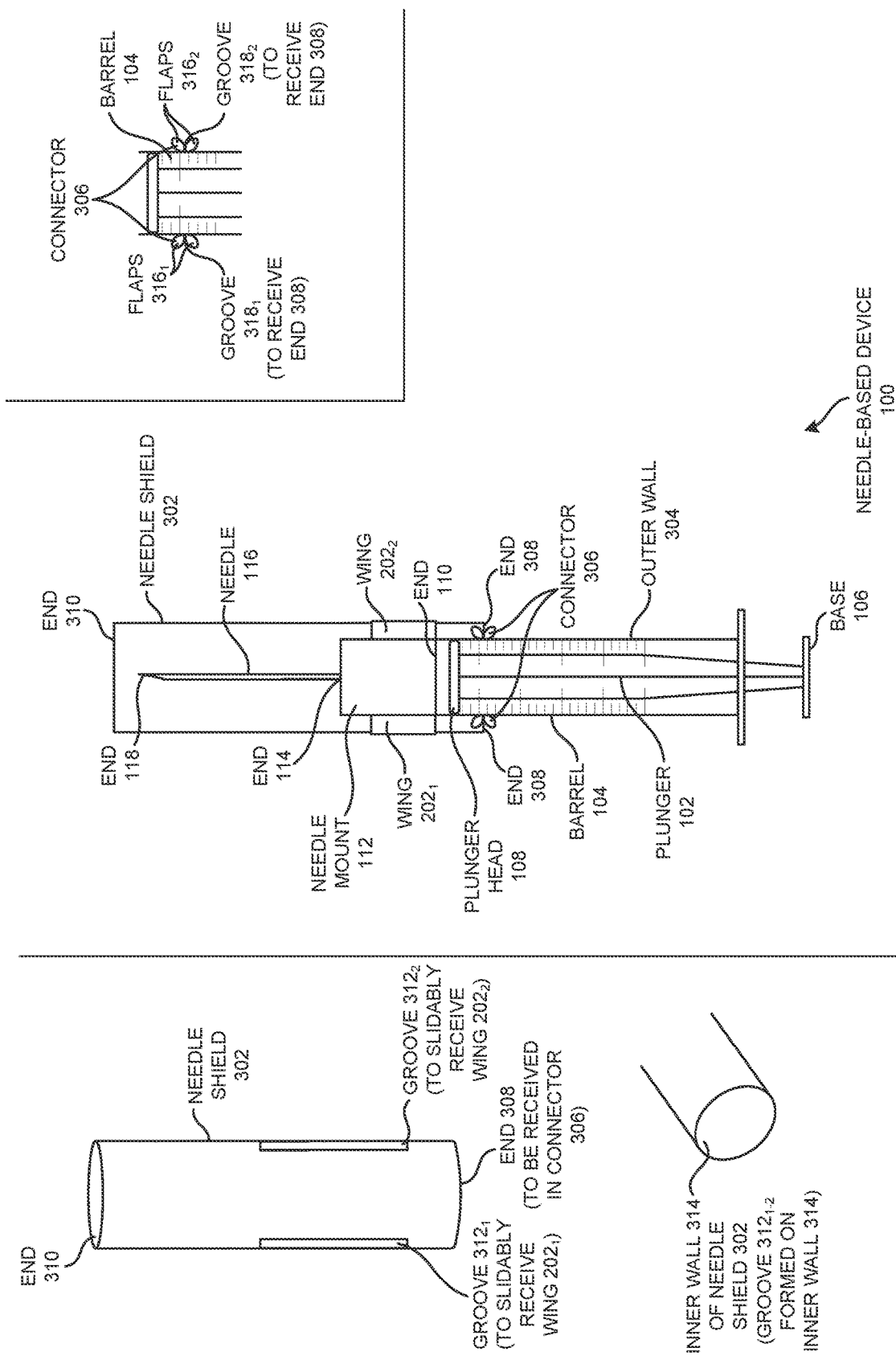
FIG. 3 is a schematic view of coupling of a needle shield to the needle-based device of FIG. 1 to encompass a needle thereof, according to one or more embodiments.

FIG. 3 shows coupling of a needle shield 302 to needle-based device 100 to encompass needle 116 thereof, according to one or more embodiments. Here, in one or more embodiments, needle shield 302 may be cylindrical or shaped like a rectangular prism/square prism based on the design of needle mount 112 and/or barrel 104. Additionally, in one or more embodiments, needle shield 302 may be hollow to enable encompassing the protruding needle 116 therewithin. In one or more embodiments, an outer wall 304 of barrel 104 proximate end 110 may have a connector 306 thereon to enable an end 308 of needle shield 302 to clasp onto connector 306 while needle shield 302 completely encompasses the protruding needle 116 therewithin. In one or more embodiments, an inner cross-sectional diameter of needle shield 302 may be more than an outer cross-sectional diameter of needle mount 112 and an outer cross-sectional diameter of barrel 104 to enable the sliding of needle shield 302 over needle mount 112 and barrel 104.

In one or more embodiments, needle shield 302 may first receive the protruding needle 116 on needle mount 112 through end 308 thereof. In one or more embodiments, needle shield 302 may then be slid over needle mount 112 until end 308 clasps onto connector 306 on outer wall 304 of barrel 104. In the state of needle shield 302 completely encompassing the protruding needle 116, the other end (e.g., end 310) of needle shield 302 may completely enclose end 118 of needle 116. FIG. 3 shows needle shield 302 to be transparent (e.g., needle shield 302 may be made of plastic, glass etc.). However, it should be noted that needle shield 302 may be translucent or opaque in certain embodiments. Here, the outer wall of needle shield 302 may include cuts (not shown) that reveal needle 116 while needle 116 is still protected by needle shield 302. All reasonable variations are within the scope of the exemplary embodiments discussed herein.

In one or more embodiments, the sliding of needle shield 302 over needle mount 112 may be facilitated by wings $202_{1-2}$ on needle mount 112. For the aforementioned purpose, optionally, grooves $312_{1-2}$ may be provided on an inner wall 314 of needle shield 302. In one or more embodiments, wings $202_{1-2}$ of needle mount 112 may be received within grooves $312_{1-2}$ during relative sliding of wings $202_{1-2}$ with respect to grooves $312_{1-2}$. While FIG. 3 shows grooves $312_{1-2}$ as cutting across inner wall 314 of needle shield 302 into an entire thickness thereof, it should be noted that grooves $312_{1-2}$ may not cut across inner wall 314 of needle shield 302 completely in one or more alternative embodiments. In one or more embodiments, needle shield 302 may slide until reception thereof within connector 306. In one or more embodiments, connector 306 may be constituted by flexible pairs of flaps $316_{1-2}$, each forming a groove $318_{1-2}$ to receive end 308 of needle shield 302 therewithin.

Thus, in one or more embodiments, user 150 may cover needle 116 with needle shield 302 for temporary protection (e.g., for transportation to a site of a patient). In one or more embodiments, needle 116 may be covered using needle shield 302 also after use thereof. In one or more embodiments, the covering of needle 116 with needle shield 302 may not only protect needle 116 but also prevent undesirable accidents arising out of unwanted contact therewith. In one or more embodiments, in order to enable injection of a fluid (e.g., a medication) into a body of a patient, needle 116 may be uncovered based on pushing needle shield 302 further downward. In one or more embodiments, as connector 306 may be flexible, user 150 may be able to apply enough downward pressure to enable end 308 of needle shield 302 to pop out of grooves $318_{1-2}$ of connector 306 and slide further downward along barrel 104. In one or more embodiments, during the course of needle shield 302 sliding further downward along barrel 104, needle 116 pops out of end 310 of needle shield 302 such that needle 116 is uncovered.

In one or more embodiments, needle shield 302 may indirectly move further downward along barrel 104 when user 150, after drawing plunger 102 outward from barrel 104, places needle shield 302 against a cap of a vial or a bottle and pushes barrel 104 inward toward the vial or the bottle. In one or more embodiments, this may automatically cause end 308 of needle shield 302 to pop out of grooves $318_{1-2}$ of connector 306 and slide further downward along barrel 104, thereby uncovering needle 116. In one or more embodiments, user 150 may hold needle shield 302 to maintain a position thereof in which needle 116 is exposed to inject a fluid (e.g., medication) into a body of a patient or extract blood therefrom. In one or more embodiments, once the task is done, a force may be applied in an opposite direction on needle shield 302 by user 150 to restore a state of complete encompassment of needle 116 by needle shield 302.

Thus, in one or more embodiments, needle-based device 100 may be provided with needle shield 302 configured to protect needle 116 in a state of disuse thereof (e.g., storage, transportation, post-injection of a fluid, post-collection of a fluid) and to be retractable to reveal needle 116 for use (e.g., injection of a fluid, collection of a fluid) thereof. It should be noted that while FIGS. 2 and 3 show wings ($202_{1-2}$, $212_{1-2}$) on lateral sides of needle mount 112, it is possible that wings may be present on lateral sides of barrel 104 instead in one or more alternative embodiments. Here, in one or more embodiments, needle mount 112 may be smaller in size and plainer. Also, it should be noted that needle shield 302 need not be coupled to barrel 104 merely by way of connector 306. In certain embodiments, needle shield 302 may merely be mounted on an element analogous to needle mount 112. In this case, said element may encompass needle mount 112 and needle shield 302 may be indirectly coupled to barrel 104 by way of being coupled to said element. In certain cases, needle mount 112 may also be interpreted as a mount (e.g., based on the element encompassing needle mount 112) for needle shield 302.

Figure 4:
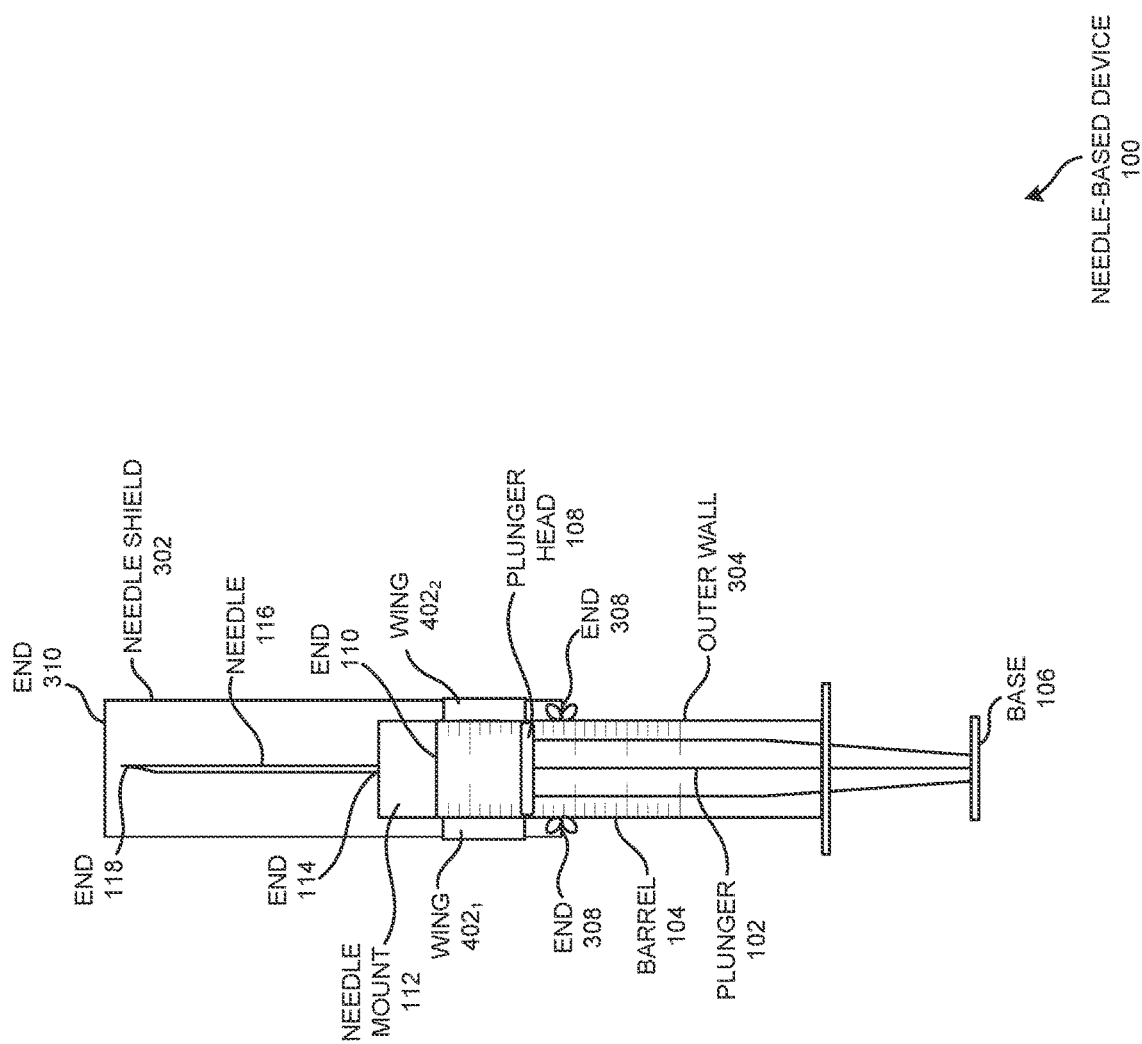
FIG. 4 is a schematic view of the needle-based device of FIG. 1 with wings on lateral sides of an outer wall of a barrel thereof, according to one or more embodiments.

FIG. 4 shows needle-based device 100 with wings $402_{1-2}$ on lateral sides of barrel 104 on outer wall 304 thereof proximate end 110, according to one or more embodiments. Here, in one or more embodiments, needle shield 302 may slide over wings $402_{1-2}$ to lock onto connector 306 on outer wall 304 to shield needle 116. In one or more embodiments, needle shield 302 may pushed further downward along barrel 104, thereby uncovering/revealing needle 116, based on pressure applied to needle shield 302 such that end 308 pops out of connector 306. Again, in one or more embodiments, needle shield 302 may be pulled back to a position in which needle shield 302 completely encompasses the protruding needle 116.

It is to be noted that while FIG. 4 shows wings $402_{1-2}$ in a configuration similar to the first configuration thereof in needle mount 112 of FIG. 2, wings $402_{1-2}$ may also be in a configuration similar to the second configuration thereof in needle mount 112 of FIG. 2. Further, all reasonable variations that allow for relative movement between needle shield 302 and needle mount 112/barrel 104 are within the scope of the exemplary embodiments discussed herein. In FIG. 4, needle mount 112 may be smaller than the embodiments of FIGS. 2-3 because of the absence of wings thereon.

Referring back to FIG. 3, it should be noted that configuration of wings $202_{1-2}$ therein may, again, not be limited. It may be possible for wings $212_{1-2}$ to be on lateral sides of needle mount 112 instead of wings $202_{1-2}$. Further, as discussed above, grooves $312_{1-2}$ may not completely cut across inner wall 314 of needle shield 302. In this embodiment, wings $212_{1-2}$ may be received within grooves $312_{1-2}$ and may slide relatively thereto. Here, the tapering on wings $212_{1-2}$ may enable needle shield 302 to be locked onto needle mount 112/barrel 104, without a requirement of connector 306. Again, needle shield 302 may be pushed downward to reveal/uncover needle 116, as discussed above. Needle shield 302 may then be manually restored to an original position thereof in which needle shield 302 completely encompasses the protruding needle 116.

Figure 5:
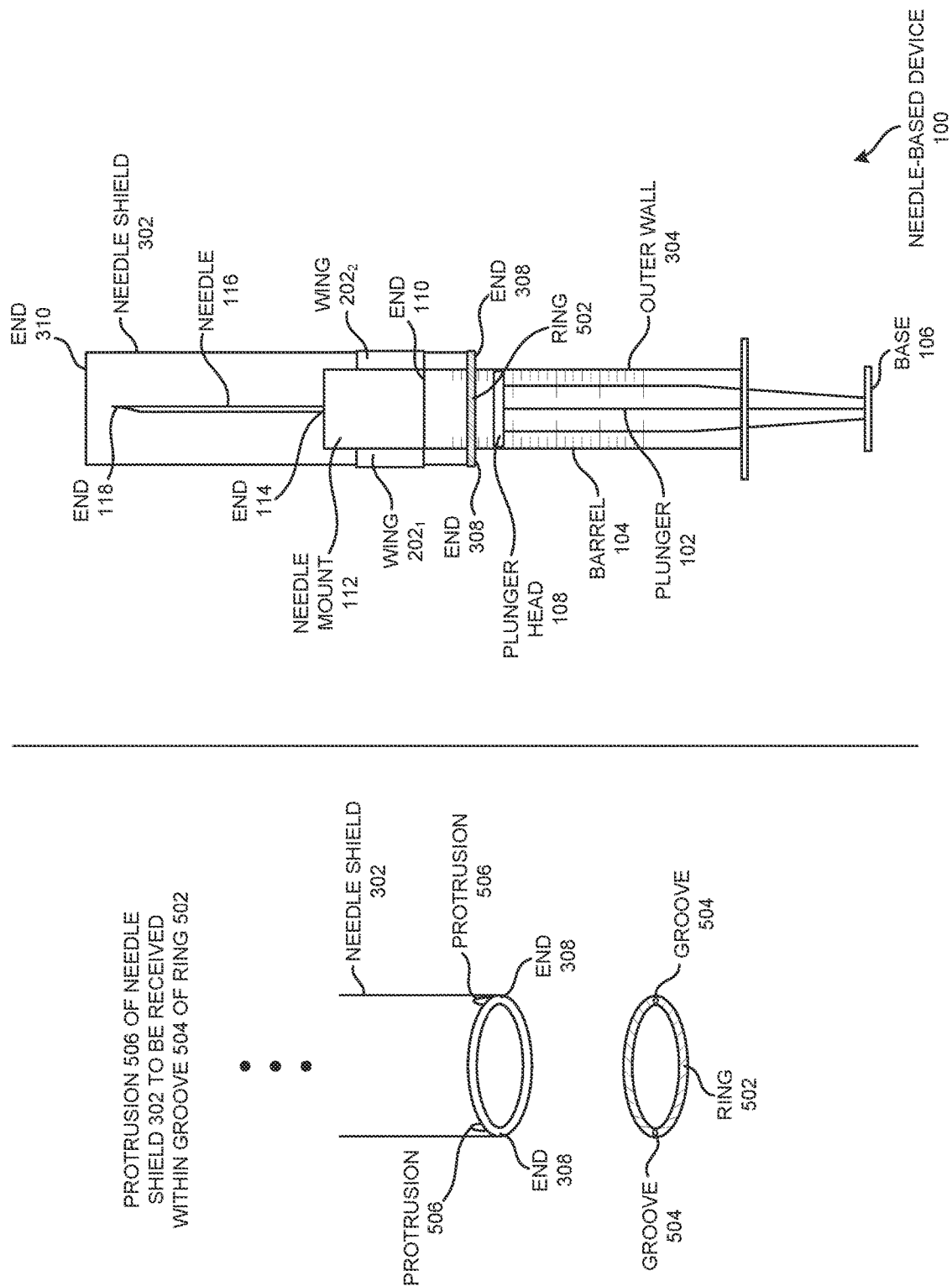
FIG. 5 is a schematic view of the needle-based device of FIG. 1 with a ring on the outer wall of the barrel thereof, according to one or more embodiments.

FIG. 5 shows needle-based device 100 with a ring 502 on outer wall 304 of barrel 104 proximate end 110, according to one or more embodiments. Here, needle mount 112 may be in the same configurations as in FIGS. 2-3; alternatively, needle mount 112 may be smaller and without any wings thereon. In one implementation, ring 502 (e.g., of uniform thickness) may protrude from outer wall 304 of barrel 104; in addition, an underside of ring 502 may have a groove 504 complementary to a protrusion 506 on end 308 of needle shield 302. Again, needle shield 302 may first receive needle 116 on needle mount 112 through end 308 thereof. Needle shield 302 may be moved downward toward barrel 104 such that, after a point, protrusion 506 of needle shield 302 locks onto groove 504 of ring 502. In this state, needle shield 302 may completely encompass the protruding needle 116 therewithin.

In one or more embodiments, ring 502 may be made of a flexible material. Also, in one or more implementations, while ring 502 may change shape due to flexibility thereof, ring 502 may not change a position thereof along barrel 104. In one or more embodiments, an appropriate downward pressure (e.g., by user 150) may enable protrusion 506 to pop out of groove 504 and cause needle shield 302 to go further downward along barrel 104. In one or more embodiments, this may uncover/reveal needle 116 for use on a patient (e.g., to extract blood, to inject a fluid, to prick a finger) or on a vial/bottle (e.g., to extract a fluid). In one or more embodiments, following use of needle 116, an upward pressure may be applied to enable protrusion 506 to once again lock into groove 504 to enable needle shield 302 completely encompass needle 116 again.

The ring (e.g., ring 502) embodiment of FIG. 5 is merely an example embodiment. Other embodiments involving rings that facilitate covering of needle 116 and uncovering thereof are within the scope of the exemplary embodiments discussed herein. In one or more embodiments, wings ($202_{1-2}$, $212_{1-2}$) on needle mount 112 may further aid the locking/unlocking/relocking of needle shield 302 at/from appropriate positions. All reasonable variations are within the scope of the exemplary embodiments discus sed herein.

Figure 6:
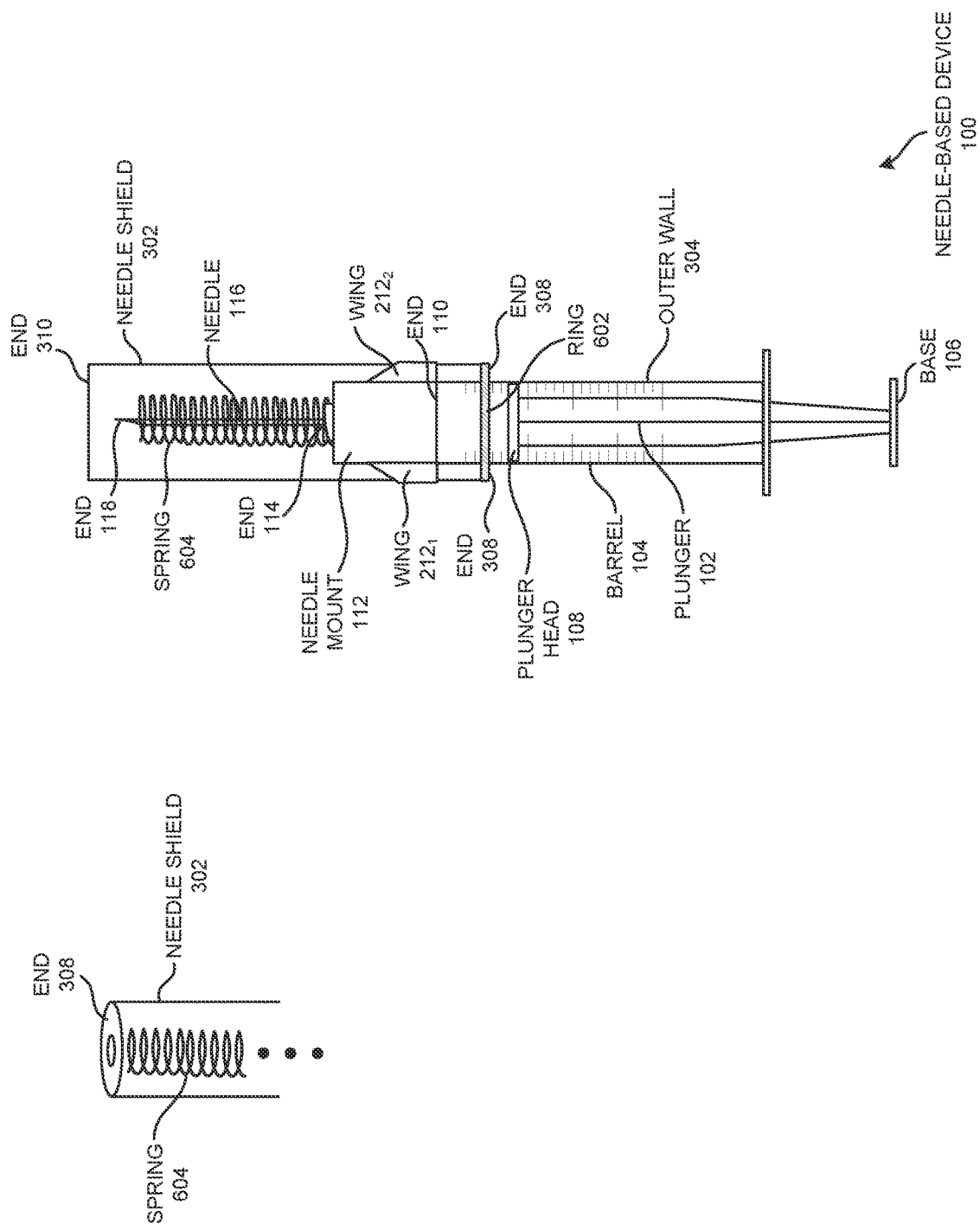
FIG. 6 is a schematic view of the needle-based device of FIG. 1 in a spring-based configuration of a needle shield thereof, according to one or more embodiments.

FIG. 6 shows needle-based device 100 in a spring-based configuration of needle shield 302, according to one or more embodiments. Here, in one or more embodiments, needle mount 112 with wings $212_{1-2}$ may be directly inserted into barrel 104 via end 110 farthest from base 106. In one example implementation, barrel 104 may have grooves (not shown) on an inside wall thereof proximate end 110 onto which needle mount 112 may be screwed. Other forms of coupling needle mount 112 to barrel 104 are within the scope of the exemplary embodiments discussed herein. In one or more embodiments, barrel 104 may have a ring 602 (e.g., analogous to ring 502, but may be structurally different; ring 602 may be made of flexible material) formed on outer wall 304 thereof proximate end 110. In some embodiments, ring 602 may be integrally formed with barrel 104, while in some other embodiments, ring 602 may be an element separate from barrel 104.

In one or more embodiments, a spring 604 may be placed over needle mount 112 such that spring 604 encompasses the protruding needle 116 along an entire length thereof. In one or more embodiments, now when spring 604 encompassing needle 116 is received within needle shield 302 through end 308 thereof and needle shield 302 is moved downward toward barrel 104, end 308 of needle shield 302 may press against ring 602. In one or more embodiments, further application of pressure (e.g., through hand 152 of user 150) may compress ring 602 and push ring 602 inside end 308 to be received within needle shield 302. In one or more embodiments, in this state, needle shield 302 may completely encompass the entire lengths of both protruding needle 116 and spring 604.

In one or more embodiments, when no further external pressure is applied, needle shield 302 may comfortably shield the protruding needle 116 and spring 602. In one or more embodiments, although ring 602 may not lock needle shield 302 in a position, needle shield 302 may be prevented from falling outward when needle-based device 100 is flipped over because a cross-sectional inner diameter of ring 602 may be more than a cross-sectional inner diameter of end 308. In one or more embodiments, needle shield 302 may be hollow. In one or more embodiments, further, a cross-sectional inner diameter of end 310 of needle shield 302 farthest away from end 308 may be smaller than a cross-sectional diameter of spring 604. Thus, in one or more embodiments, needle shield 302 may be prevented from falling downward by spring 604 when needle-based device 100 is held in an upright position.

In one or more embodiments, if spring 604 were not present, needle shield 302 may slip and fall downward; alternatively or additionally, needle shield 302 may be prevented from falling downward based on an element mounted on needle mount 112, as discussed above. However, in one or more embodiments, upon further application of pressure in a downward direction toward barrel 104 by user 150 or by pressing end 310 of needle shield 302 against a surface (e.g., an arm of a patient, a cap of a vial/bottle) that exerts a normal reaction in the downward direction, needle shield 302 moves in the downward direction along barrel 104, thereby compressing spring 604 also in the same direction to uncover/reveal needle 116. In one or more embodiments, the uncovered/revealed needle 116 may then be utilized appropriately (e.g., for injecting a fluid into a patient, for pricking a finger/body part of the patient, for pricking a cap of a vial/bottle). Following use of needle 116, the force along the direction of compression of spring 604 may be relaxed (e.g., by taking needle-based device 100 out of the surface, user 150 stopping the application of pressure in the downward direction) to enable spring 604 revert to an uncompressed version thereof; in the uncompressed state of spring 604, needle shield 302 may once again completely encompass the protruding needle 116 and spring 604.

In other words, immediately following relaxation of the application of the force along the direction of compression of spring 604, needle-based device 100 may be automatically transitioned back to the state of disuse thereof (e.g., a state where needle shield 302 completely encompasses needle 116 and spring 604) following use thereof in accordance with another force (e.g., a restoring force) provided by decompression of spring 604 that is automatically applied in a direction diametrically opposite to the direction of compression of spring 604.

In the scenario of injecting a fluid into the body of a patient, needle-based device 100 may first be placed against a cap of a vial/bottle from which the fluid is to be extracted. When end 310 is pressed against the cap, the normal reaction from the cap pushes needle shield 302 downward, thereby compressing spring 604. The downward movement of needle shield 302 and the compression of spring 604 exposes needle 116 that pricks the cap. Plunger 102 may also be pushed in by way of user 150 pressing base 106 in an upward direction toward needle mount 112 such that plunger head 108 contacts needle mount 112. Now, pulling plunger 102 back may create a gap between needle mount 112 and plunger head 108. Said gap may constitute a low pressure region, thereby enabling the fluid to fill the gap by way of gushing in through the hollow needle 116.

Now, the desired quantity of the fluid may be filled in the gap. The gap may be controlled based on graduated marks (e.g., shown as graduated marks 606) on barrel 104. Once the desired quantity of fluid is available in the gap, user 150 may take needle-based device 100 out of the vial/bottle, thereby decompressing spring 604 to restore spring 604 to the original shape thereof. User 150 may then place end 310 of needle shield 302 against the arm of a patient, which, again, compresses spring 604 as discussed above, and exposes needle 116. The exposed needle 116 may prick a skin of the patient; the pressing of base 106 may compress a volume of the gap, thereby creating a high pressure region therein. The fluid may be squeezed through the hollow needle 116 into the body of the patient.

Once the fluid is injected into the body of the patient, needle-based device 100 may be extracted out of the arm of the patient. This decompresses spring 604 and restores needle shield 302 to the position in which needle shield 302 completely encompasses the exposed needle 116 and spring 604. Needle-based device 100 may also be employed to prick a finger tip of the patient to extract blood or to extract another fluid from a bottle/vial; additionally, needle-based device 100 may be used to extract venom from a body portion of a mammal. The details with respect to the figures discussed above make the aforementioned uses obvious. All reasonable variations are within the scope of the exemplary embodiments discussed herein.

With respect to FIG. 6, it is obvious that needle shield 302 may be retracted to reveal needle 116 and released to close needle 116 at will. Also, wings $212_{1-2}$ on needle mount 112 may aid the secure coupling between needle shield 302 and barrel 104. It is possible to envision the embodiment of FIG. 6 without wings $212_{1-2}$. To summarize, the embodiment of FIG. 6 may be employed in two distinct modes of operation with respect to the use of needle-based device 100 where needle shield 302 is retracted to compress spring 604 and to reveal needle 116. In one or more embodiments, the first distinct mode of operation of use of needle-based device 100 may be the extraction of a fluid from a vial/bottle or a body (e.g., arm) of a mammal (e.g., a human), and the second distinct mode of operation of use of needle-based device 100 may be the injection of said fluid into the body of the mammal or a body of another mammal. No current solutions exist where an analogous needle is shielded and exposed for use during both the extraction of a fluid and the injection thereof. Yet another mode of operation of the embodiment of FIG. 6 may be related the state of disuse of needle-based device 100 where needle 116 is completely shielded/encompassed by spring 604 and needle shield 302.

Figure 7:
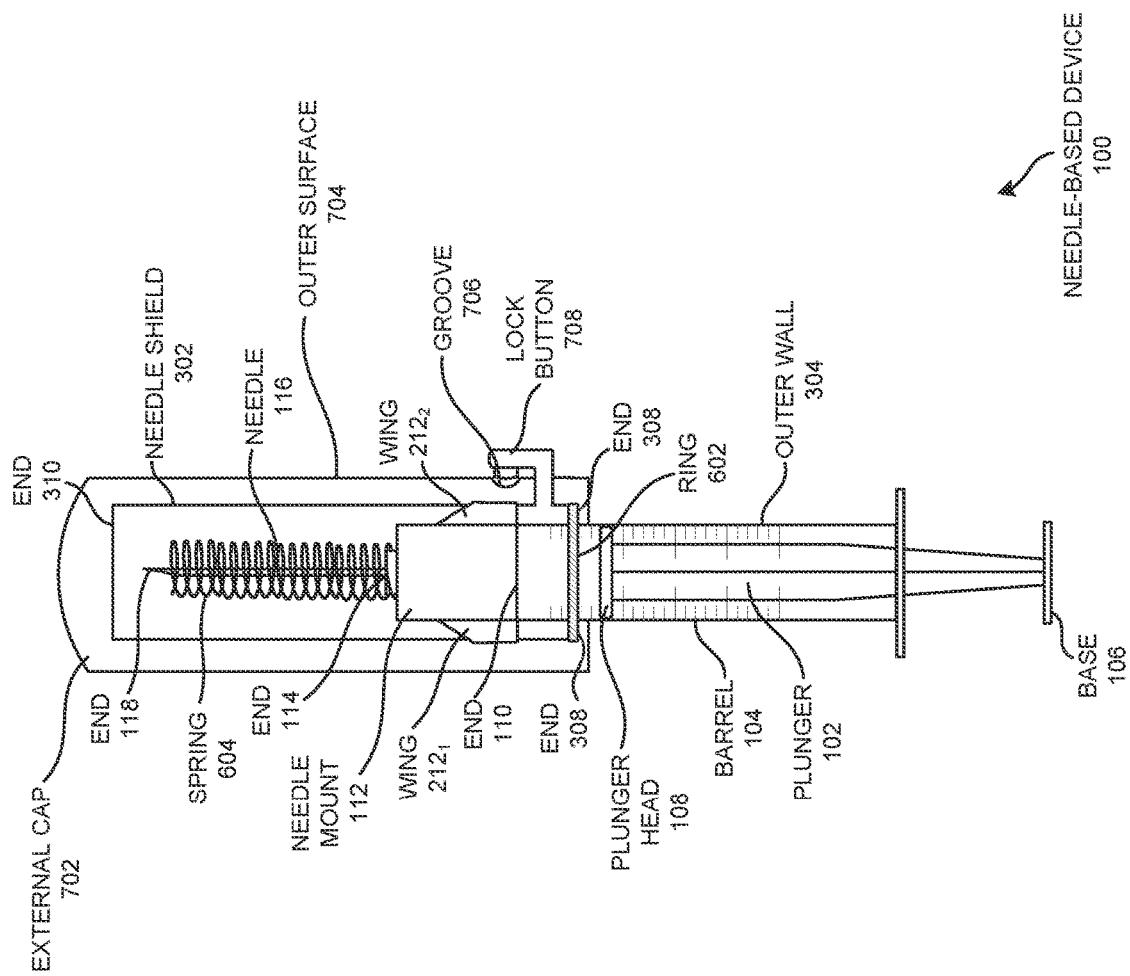
FIG. 7 is a schematic view of an external cap configured to at least partially cover the needle shield of the needle-based device of FIGS. 1 and 3, according to one or more embodiments.

FIG. 7 shows an external cap 702 configured to at least partially cover needle shield 302, according to one or more embodiments. In one or more embodiments, external cap 702 may be made of a transparent (e.g., plastic, glass), a translucent (e.g., rubber) or an opaque material to cover the slits and cuts on needle shield 302. In one or more embodiments, an outer surface 704 of external cap 702 may have a groove 706 therein. Correspondingly, in one or more embodiments, needle shield 302 may have a lock button 708 on an outer surface thereof. In one or more embodiments, lock button 708 of needle shield 302 may be configured to be received into groove 706 on external cap 702 to lock needle-based device 100 (e.g., in a state of disuse thereof).

In one or more embodiments, the use of external locking may prevent reuse of needle-based device 100, or at least needle 116 therein. Although FIG. 7 shows needle shield 302 as covering needle 116 and spring 604, concepts associated with the external locking may also be applicable across the embodiments of FIGS. 1-5. In one or more embodiments, the external locking may prevent movement of needle shield 302, which, in turn, prevents reuse of needle-based device 100. Alternatively, needle shield 302 itself may include both lock button 708 and groove 706. Here, locking may be done merely using elements of needle shield 302. In another alternative implementation, lock button 708 may be external to needle shield 302. For example, lock button 708 may be on external cap 702 and groove 706 may be on needle shield 302. Here, lock button 708 of external cap 702 may be received within groove 706 of needle shield 302.

In yet another alternative implementation, external cap 702 may cover lock button 708 of needle shield 302 to prevent premature/accidental locking during transportation or handling of needle-based device 100. In one example implementation, external cap 702 may be designed like a pen cap. Other configurations of external cap 702 are within the scope of the exemplary embodiments herein.

Thus, exemplary embodiments discussed above provide for safety mechanisms with respect to needle-based device 100. The manual shielding available in typical syringes may require capping a needle after use thereof. The capping and uncapping may cause needle injuries to a user. Additionally, in a spring-based typical implementation of a syringe that allows for a needle to be retracted therewithin, some space may be reserved in a barrel for the spring. This may result in loss of space for medication. The automatic retraction of needle shield 302 in the exemplary embodiments discussed herein may also allow for one-handed operation of needle-based device 100. All reasonable variations are within the scope of the exemplary embodiments discussed herein.

It should be noted that exemplary embodiments discussed above have been placed in the context of a syringe and needle 116, with barrel 104 and plunger 102. However, concepts associated with the exemplary embodiments discussed herein are applicable across embodiments where needle mount 112 is coupled to a body (alternative to barrel 104) of needle-based device 100 and needle 116 protrudes from needle mount 112. In one or more embodiments, needle shield 302 may encompass the protruding needle 116 in a state of operation; needle shield 302 may be retracted to reveal/uncover needle 116. In one or more embodiments, needle shield 302 may also be protected through external cap 702, as discussed above. All reasonable variations in and combinations of the exemplary embodiments discussed with respect to FIGS. 1-7 are within the scope of the exemplary embodiments discussed herein.

Figure 8:
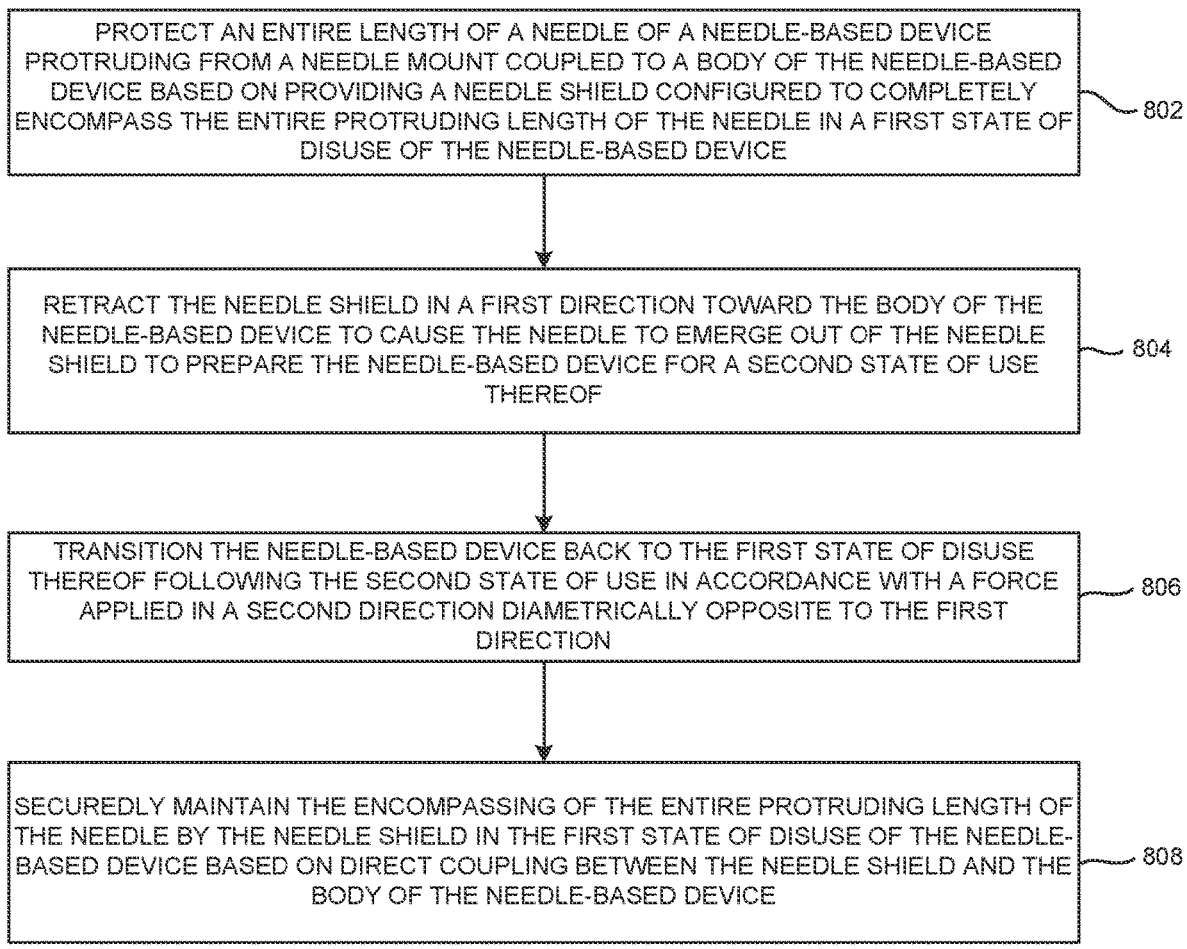
FIG. 8 is a process flow diagram detailing the operations involved in implementing a security mechanism in the needle-based device of FIG. 1, according to one or more embodiments.

FIG. 8 shows a process flow diagram detailing the operations involved in implementing a security mechanism in a needle-based device (e.g., needle-based device 100), according to one or more embodiments. In one or more embodiments, operation 802 may involve protecting an entire length of a needle (e.g., needle 116) of the needle-based device protruding from a needle mount (e.g., needle mount 112) coupled to a body (e.g., barrel 104) of the needle-based device based on providing a needle shield (e.g., needle shield 302) configured to completely encompass the entire protruding length of the needle in a first state of disuse of the needle-based device. In one or more embodiments, operation 804 may involve retracting the needle shield in a first direction toward the body of the needle-based device to cause the needle to emerge out of the needle shield to prepare the needle-based device for a second state of use thereof.

In one or more embodiments, operation 806 may involve transitioning the needle-based device back to the first state of disuse thereof following the second state of use in accordance with a force applied in a second direction diametrically opposite to the first direction. In one or more embodiments, operation 808 may then involve securedly maintaining the encompassing of the entire protruding length of the needle by the needle shield in the first state of disuse of the needle-based device based on coupling between the needle shield and the body of the needle-based device.

Figure 9:
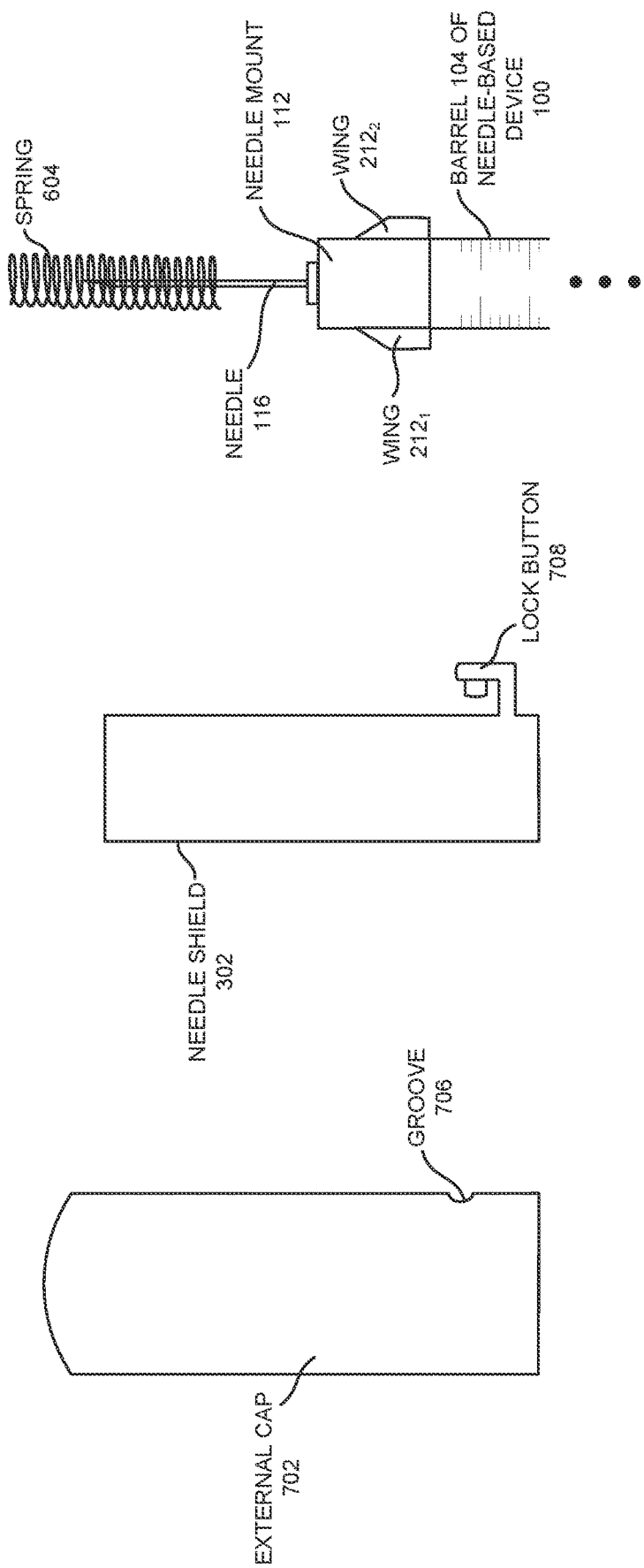
FIG. 9 is a schematic view of the spring-based embodiment of FIGS. 6-7 with external cap, needle mount and needle shield thereof as modular elements.

FIG. 9 shows the spring-based embodiment of FIGS. 6-7 with external cap 702, needle mount 112 and needle shield 302 as modular elements. In one or more embodiments, as clearly indicated by FIGS. 6 and 9 and as discussed above, needle shield 302 may be mounted onto barrel 104 (body of needle-based device 100) directly or, for example, through the user of a connector (such as ring 602) such that needle shield 302 encompasses both spring 604 and needle 116. As discussed with reference to FIG. 6, the relative cross-sectional areas/diameters of needle mount 112, needle shield 302 and ring 602 may automatically enable protection of needle 116 and prevent accidental sticks caused by needle 116 otherwise. It should be noted that there may be snaps (not shown) formed on barrel 104 (or body of needle-based device 100) to enable direct coupling of needle shield 302 thereonto.

Figure 10:
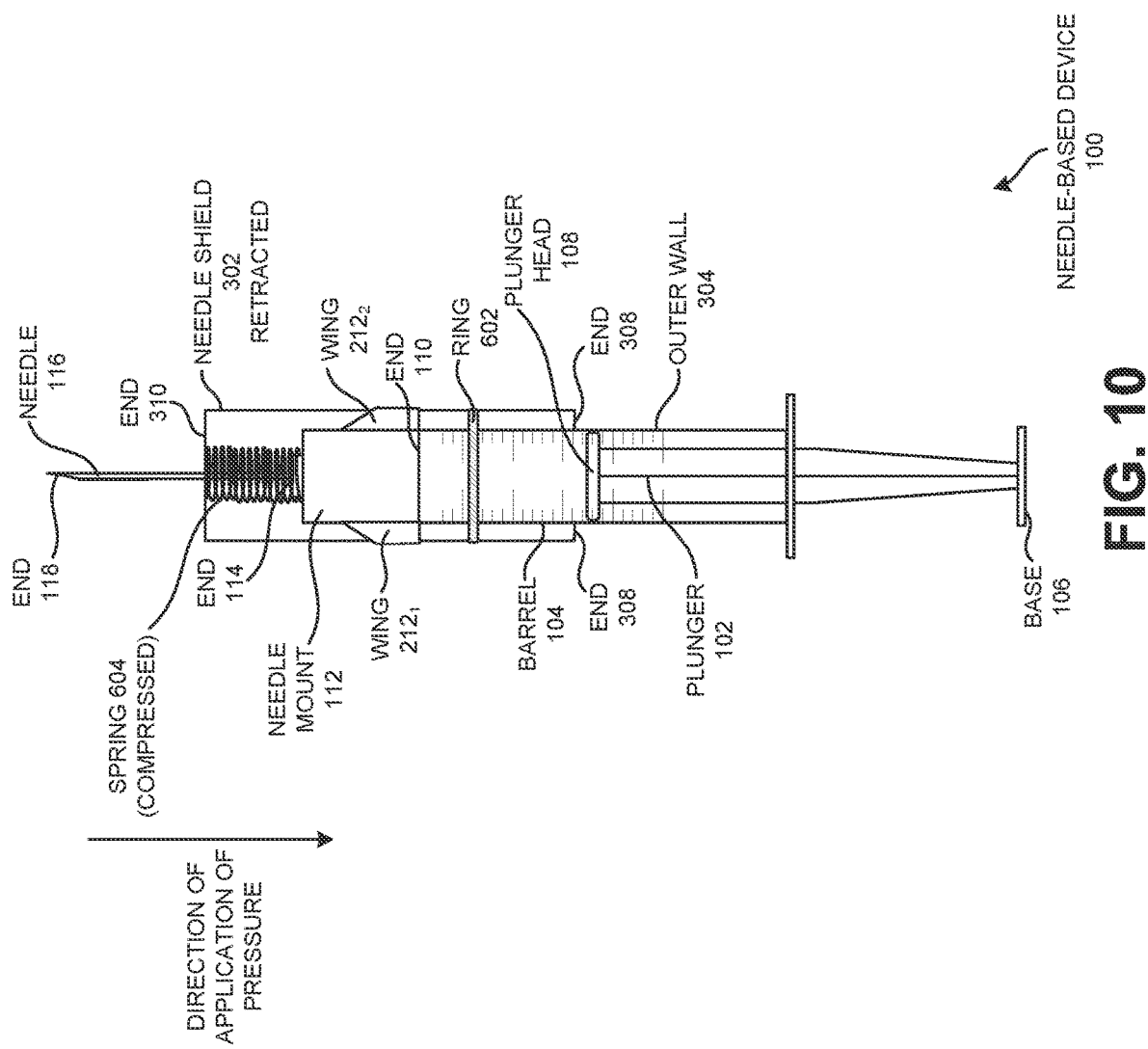
FIG. 10 is an illustrative view of retraction of the needle shield in the spring-based embodiment of FIG. 6.
Figure 11:
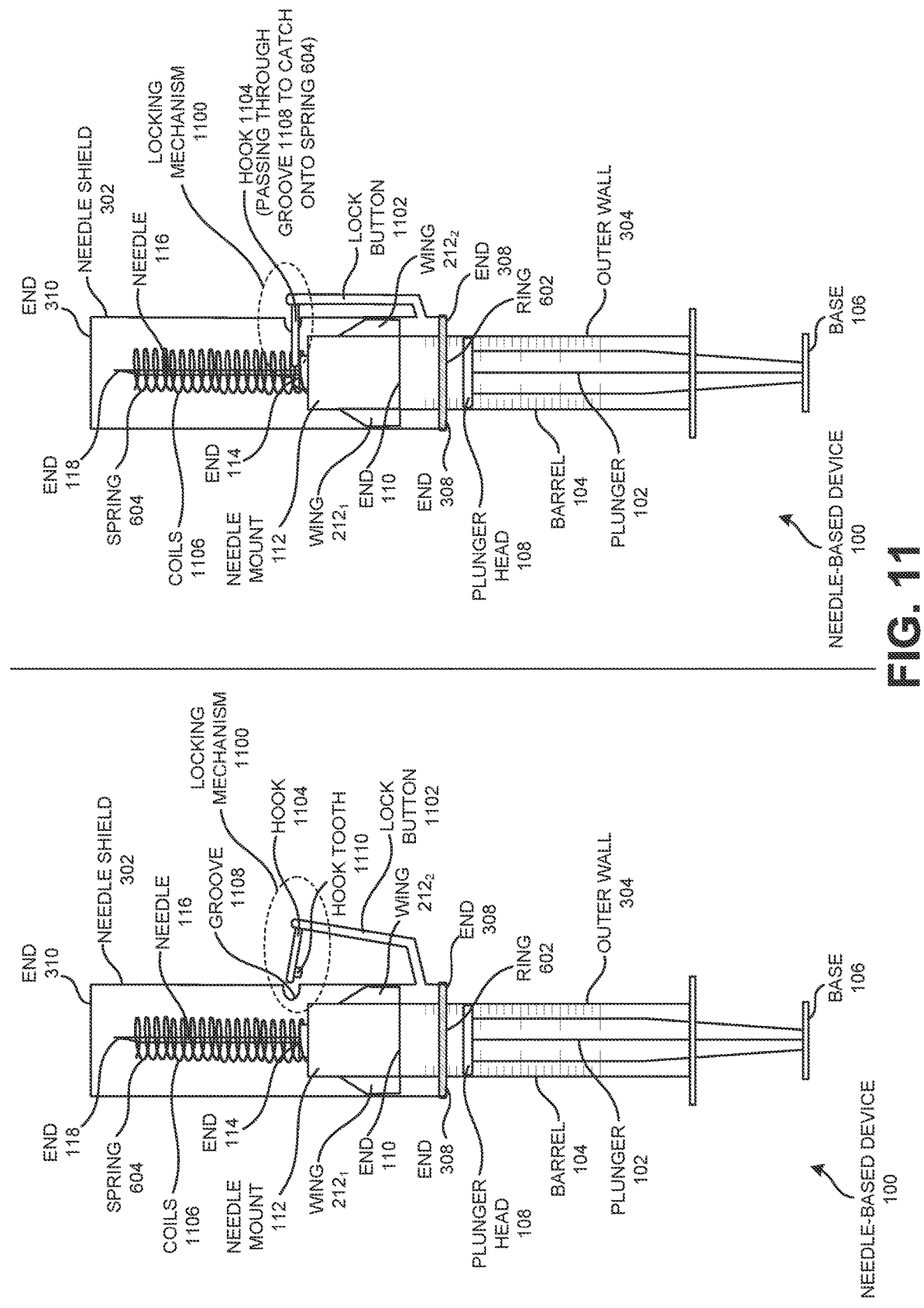
FIG. 11 is a schematic view of a locking mechanism of a needle-based device in accordance with the embodiments of FIGS. 6 and 7, but as a variant thereof.

FIG. 10 shows retraction of needle shield 302 in the spring-based embodiment of FIG. 6, according to one or more embodiments. As discussed above, once pressure is applied in a downward direction toward barrel 104 by user 150 or by pressing end 310 of needle shield 302 against a surface (e.g., an arm of a patient, a cap of a vial/bottle), needle shield 302 moves in the same downward direction, thereby compressing spring 604 as shown in FIG. 10. FIG. 11 shows a locking mechanism 1100 of needle-based device 100 in accordance with the embodiments of FIGS. 6 and 7, but as a variant thereof. Here, in one or more embodiments, locking mechanism 1100 may include a lock button 1102 (analogous to lock button 708) on needle shield 302 on a location proximate to end 114/top of needle mount 112; however, here, lock button 1102 may have a hook 1104 thereon configured to get between coils 1106 of spring 604 to touch the top of needle mount 112 and lock needle shield 302 by way of a hook tooth 1110 on hook 1104 catching onto one or more wire(s) of spring 604, as shown in FIG. 11; for the aforementioned purpose, needle shield 302 may have a groove 1108 on an outer wall thereof through which hook 1104 and hook tooth 1110 pass to lock into coils 1106 of spring 604 and the top of needle mount 112. This increases the lock force compared to the lock force in the embodiment of FIG. 7, where lock button 708 engages with external cap 702 instead.

Figure 12:
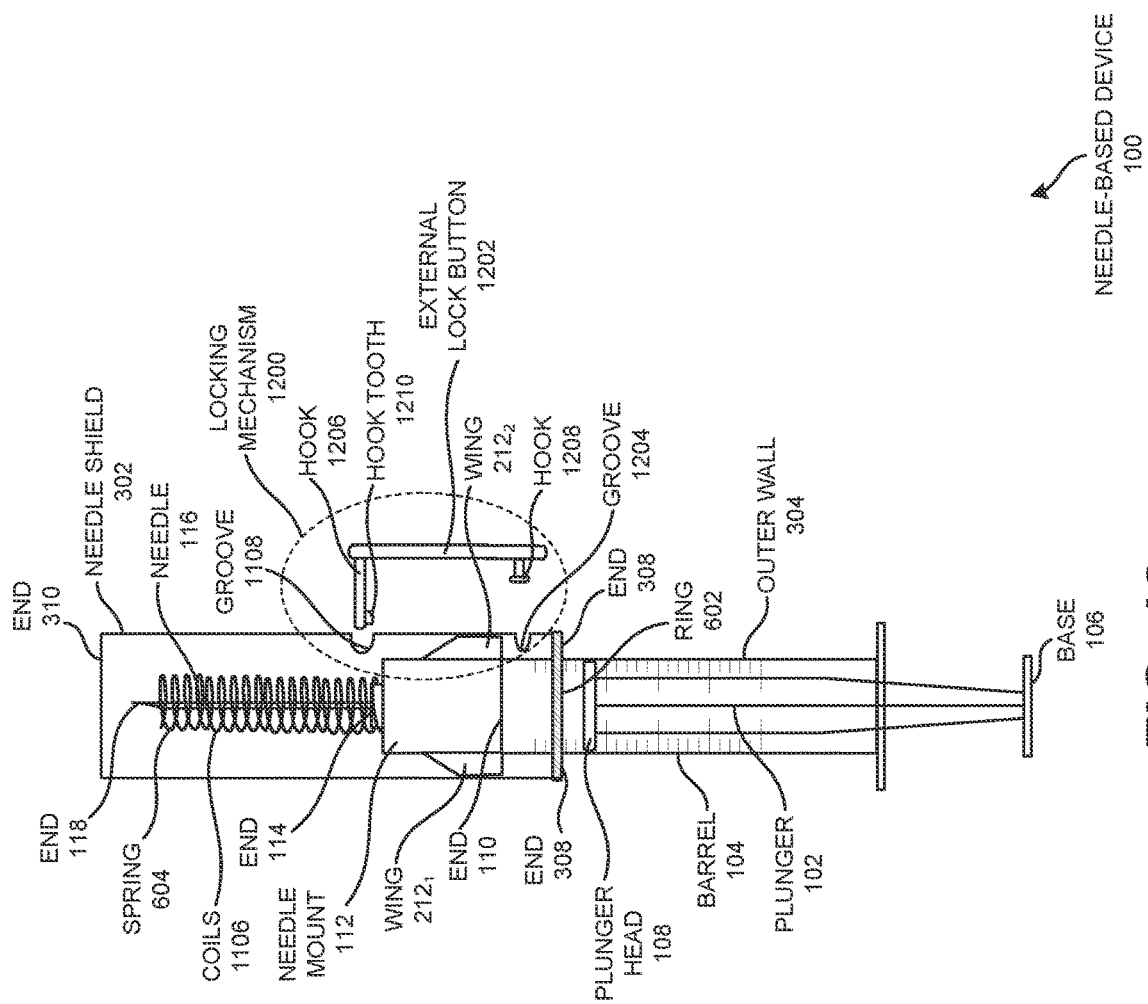
FIG. 12 is a schematic view of an external lock button utilized in the needle-based device of FIG. 6.

As discussed above, other possible embodiments include lock button 708 being a separate element that engages with needle shield 302 or both with needle shield 302 and spring 604. FIG. 12 shows an external lock button 1202 (e.g., part of locking mechanism 1200) that is configured to engage both with a groove 1204 on needle shield 302 (e.g., by way of a hook 1208 on external lock button 1202) and coils 1106 (e.g., through groove 1108 by way of another hook 1206 including a hook tooth 1210 on external lock button 1202) of spring 604. Again, the embodiment context of external lock button 1202 is similar to that of FIG. 6. In one or more embodiments, spring 604 discussed above may be a separate element or integrated with needle mount 112 discussed above or needle shield 302. In one or more embodiments, spring 604 may be a metal spring or molded spring. In one or more embodiments, needle shield 302 across all embodiments, along with other elements such as needle mount 112 and spring 604, may be sold as a safety mechanism distinct from a syringe or another form of needle-based device 100.

Figure 13:
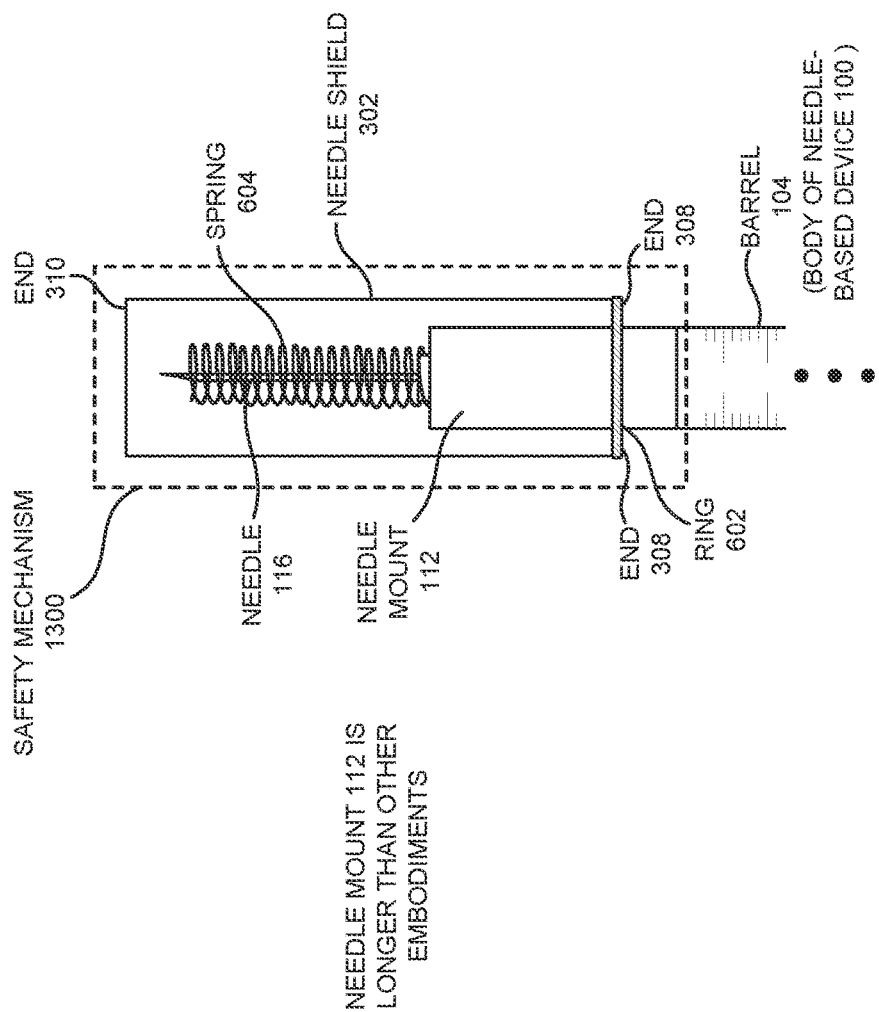
FIG. 13 is an illustrative view of a safety mechanism of the needle-based device of FIG. 6, with a longer needle mount.

FIG. 13 shows the embodiment of FIG. 6, but with a longer needle mount 112. Here, needle mount 112 may be longer such that ring 602 may be formed thereon instead of barrel 104. Thus, needle 116 with needle mount 112 and needle shield 302 may be sold as a separate safety mechanism 1300 distinct from needle based device 100. It should be noted that the manual embodiment of FIG. 3 also can include the lock mechanisms (e.g., those of FIG. 7 and FIGS. 11-12 (without catching wires of spring 604 as spring 604 does not exist in the embodiment of FIG. 3); it is easy to envision the embodiment of FIG. 7 without spring 604) discussed herein. All reasonable variations are within the scope of the exemplary embodiments discussed herein. Also, it should be noted that mechanisms of injection of a fluid into a body of a mammal and extraction of a fluid from a vial/bottle/body of the mammal are known to one skilled in the art, especially with regard to needle-based device 100. Detail discussion and illustration thereof are, therefore, skipped for the sake of convenience and clarity.

Figure 14:
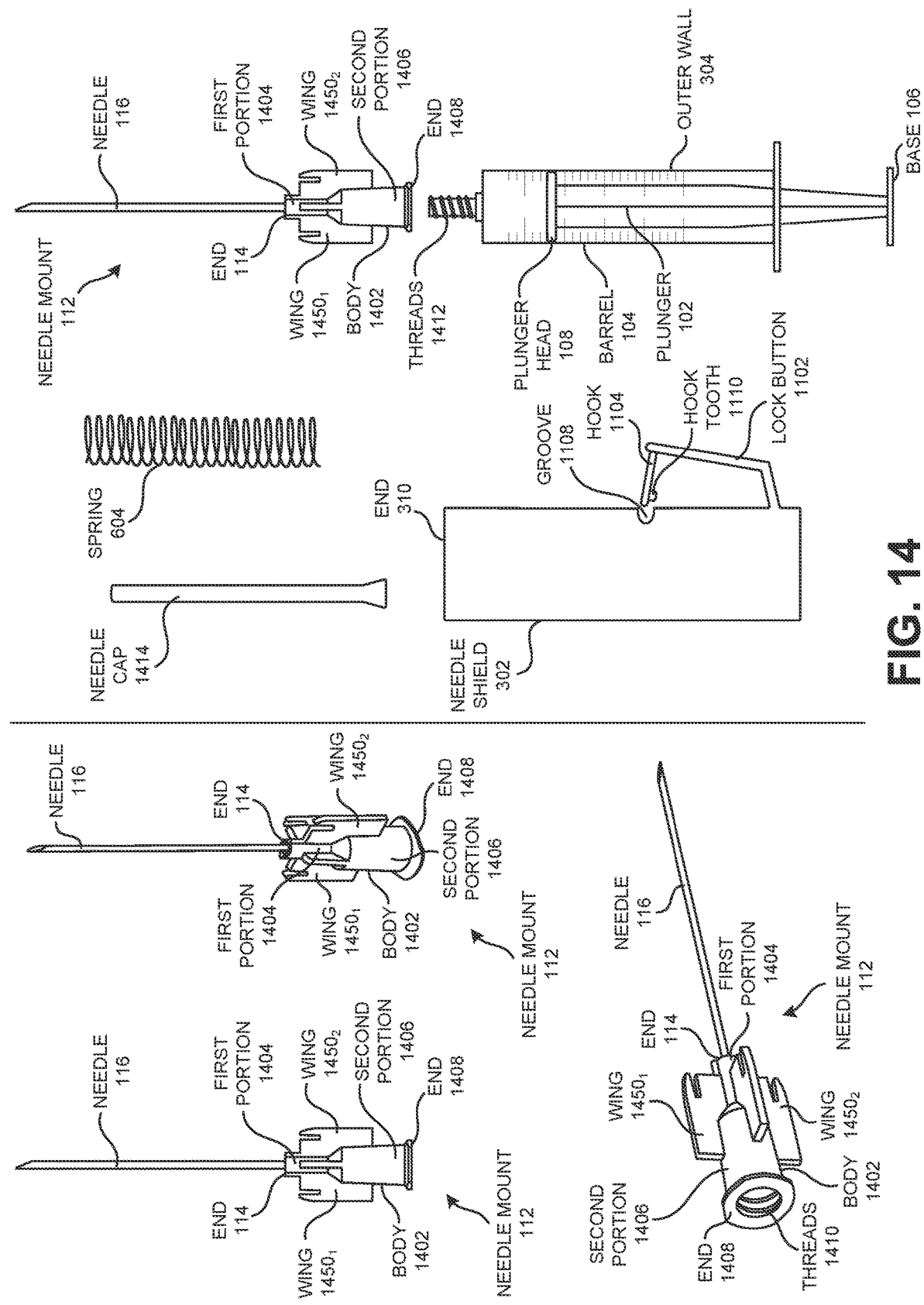
FIG. 14 is a schematic view of another embodiment of the needle mount of the needle-based device of FIGS. 1-7 and 9-13.

FIG. 14 shows yet another embodiment of needle mount 112, according to one or more embodiments. Here, needle mount 112 may have end 114 thereof to which needle 116 is to be attached. Starting from end 114, a body 1402 of needle mount 112 may have a narrow first portion 1404 (e.g., cylindrical) configured to receive needle 116 through end 114. Said cylindrical first portion 1404 may open out into a wider second portion 1406 (e.g., again, cylindrical) that continues till another end 1408 of needle mount 112 opposite to end 114.

As shown in FIG. 14, second portion 1406 may be threaded (e.g., with threads 1410) on an undersurface (e.g., inner surface) thereof. FIG. 14 also shows barrel 104 being threaded (e.g., with threads 1412) around an end (e.g., end 110) thereof. Threads 1410 of second portion 1406/needle mount 112 and threads 1412 of barrel 104 may be complementary to one another such that needle mount 112 is coupled to barrel 104 by way of needle mount 112 being screwed onto barrel 104 by way of threads 1410 and threads 1412. The design of needle mount 112 with a hollow and narrow first portion 1404 and wider second portion 1406 may enable needle 116 to approximately reach second portion 1406 from one side and barrel 104 to approximately reach first portion 1404 from the other following coupling between needle mount 112 and barrel 104. Obviously, needle mount 112 may include wings $1450_{1-2}$ on lateral sides of first portion 1404 and second portion 1406 to enable needle mount 112 move along inner walls of needle shield 302 which may/may not include grooves (e.g., analogous to grooves $312_{1-2}$ of FIG. 3) to facilitate the aforementioned movement.

Several embodiments may be possible. In one embodiment, second portion 1406 may be tapered in a direction toward first portion 1404. In other words, second portion 1406 may be widest at end 1408 and narrowest when closest to first portion 1404. Here, around the end (e.g., end 110) discussed above, barrel 104 may be tapered in a manner complementary to the tapering of second portion 1406. Second portion 1406 may be non-tapered in another embodiment. In yet another embodiment, threads 1412 may be on an inner surface/inner wall of barrel 104 and threads 1410 may be on an outer surface of second portion 1406. The coupling of needle mount 112 to barrel 104 may then involve screwing needle mount 112 into barrel 104. Further, in another embodiment, the tapered portion of barrel 104 may be a modular element in itself that is replaceable with another tapered portion. All reasonable variations are within the scope of the exemplary embodiments discussed herein.

As discussed above, as needle 116 approximately reaches second portion 1406 from one side when coupled to needle mount 112 and barrel 104 approximately reaches first portion 1404 of needle mount 112 when barrel 104 is coupled to needle mount 112, the design of needle mount 112 may ensure that the dead space for fluid loss is minimized. FIG. 14 also shows an example means of coupling between barrel 104 and needle mount 112 of needle-based device 100, according to one or more embodiments. Obviously, spring 604 and needle shield 302 in various configurations thereof discussed above may be part of needle-based device 100 in the embodiments disclosed and anticipated by FIG. 14.

Figure 15:
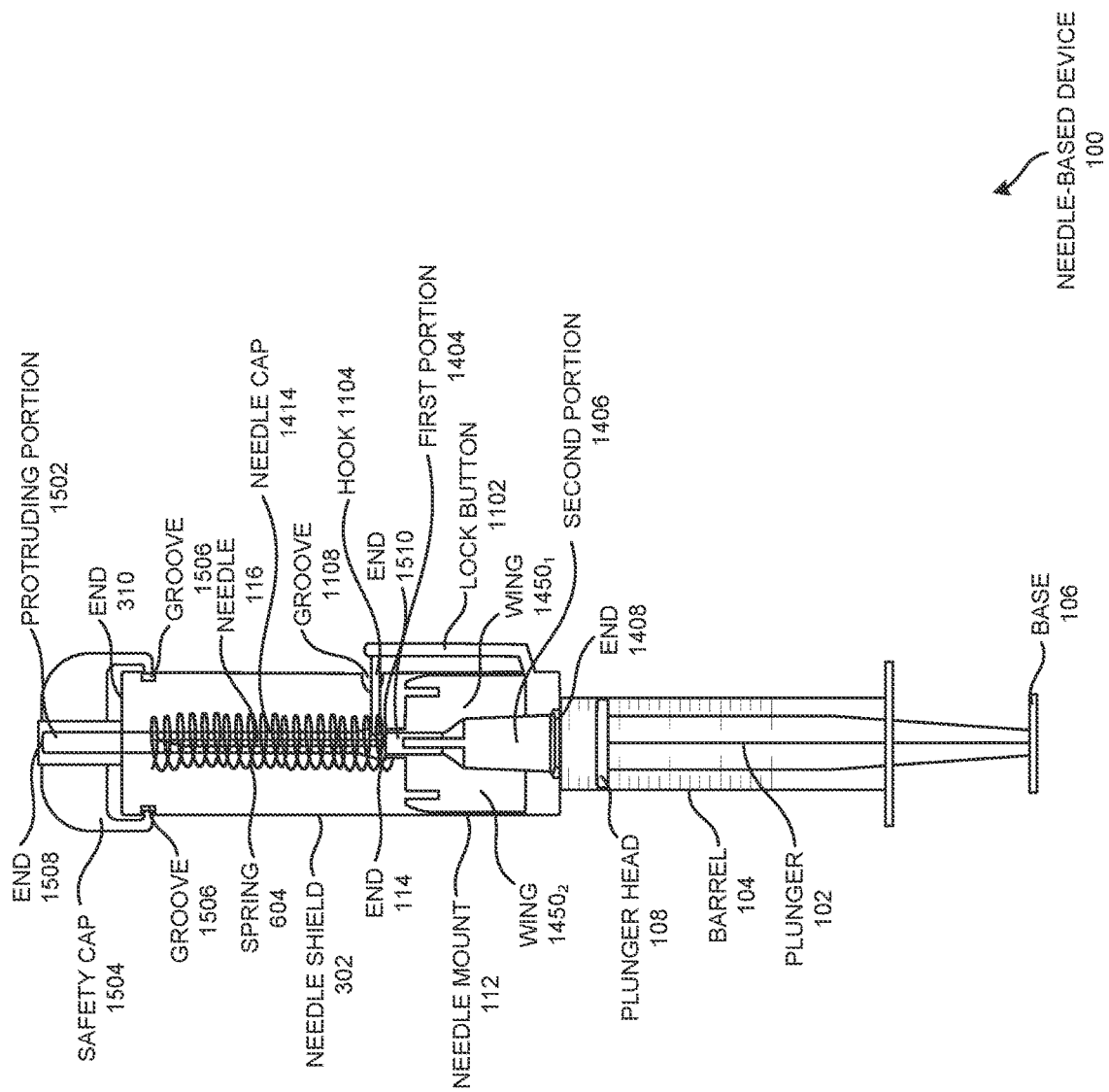
FIG. 15 is a schematic view of a needle-based device analogous to the needle-based device of FIGS. 1-7 and 9-13 in a state of disuse thereof in accordance with the embodiment of the needle mount of FIG. 14.

In one or more embodiments, as shown in FIG. 14, needle-based device 100 may further include a needle cap 1414 configured to cover needle 116 in a state of disuse thereof. FIG. 15 shows needle-based device 100 in accordance with the embodiment of FIG. 14 in a state of disuse thereof, according to one or more embodiments. Needle shield 302 is shown as transparent for the sake of illustrative convenience. In one or more embodiments, needle-based device 100 may include needle 116 completely covered with needle cap 1414 in the state of disuse thereof. As seen in the spring embodiments of FIGS. 6-7 and FIGS. 9-13, needle 116, in turn, may be completely encompassed by spring 604 in the state of disuse of needle-based device 100; needle cap 1414 covering needle 116 may at least be partially encompassed by spring 604.

It is easily possible to envision embodiments discussed herein without spring 604, but exemplary embodiments discussed herein include spring 604 for the sake of convenience. In one or more embodiments, needle cap 1414 may be a hollow cylindrical or tapered element to accommodate needle 116 therewithin. In one or more embodiments, in the state of disuse of needle-based device 100, needle shield 302 may completely encompass needle 116 and spring 604 therewithin. In one or more embodiments, needle shield 302 may also completely encompass needle cap 1414 therewithin, save for a small portion (e.g., protruding portion 1502) that protrudes out of needle shield 302 (e.g., out of end 310). In one or more embodiments, protruding portion 1502 may be covered with a safety cap 1504 that clings onto grooves 1506 on an outer surface of needle shield 302 such that safety cap 1504 is coupled to needle shield 302 and covers protruding portion 1502 of needle cap 1414 completely. It should be noted that the uncompressed spring 604 completely encompasses needle 116 (and partially encompasses needle cap 1414) in this state of disuse of needle-based device 100.

In one or more embodiments, the presence of safety cap 1504 ensures that needle cap 1414 is kept stable and that needle 116 within is completely covered by needle cap 1414 in the state of disuse of needle-based device 100. Further, if needle cap 1414 includes a hole on an end 1508 thereof farthest to needle mount 112, needle 116 may not pop out of needle shield 302 in case of needle 116 accidentally disengaging from needle mount 112 in the state of disuse of needle-based device 100. FIG. 15 also shows needle cap 1414 locking onto needle mount 112 at end 1510 thereof; said coupling may be based on threads (not shown) or any other possible means therefor.

Figure 16:
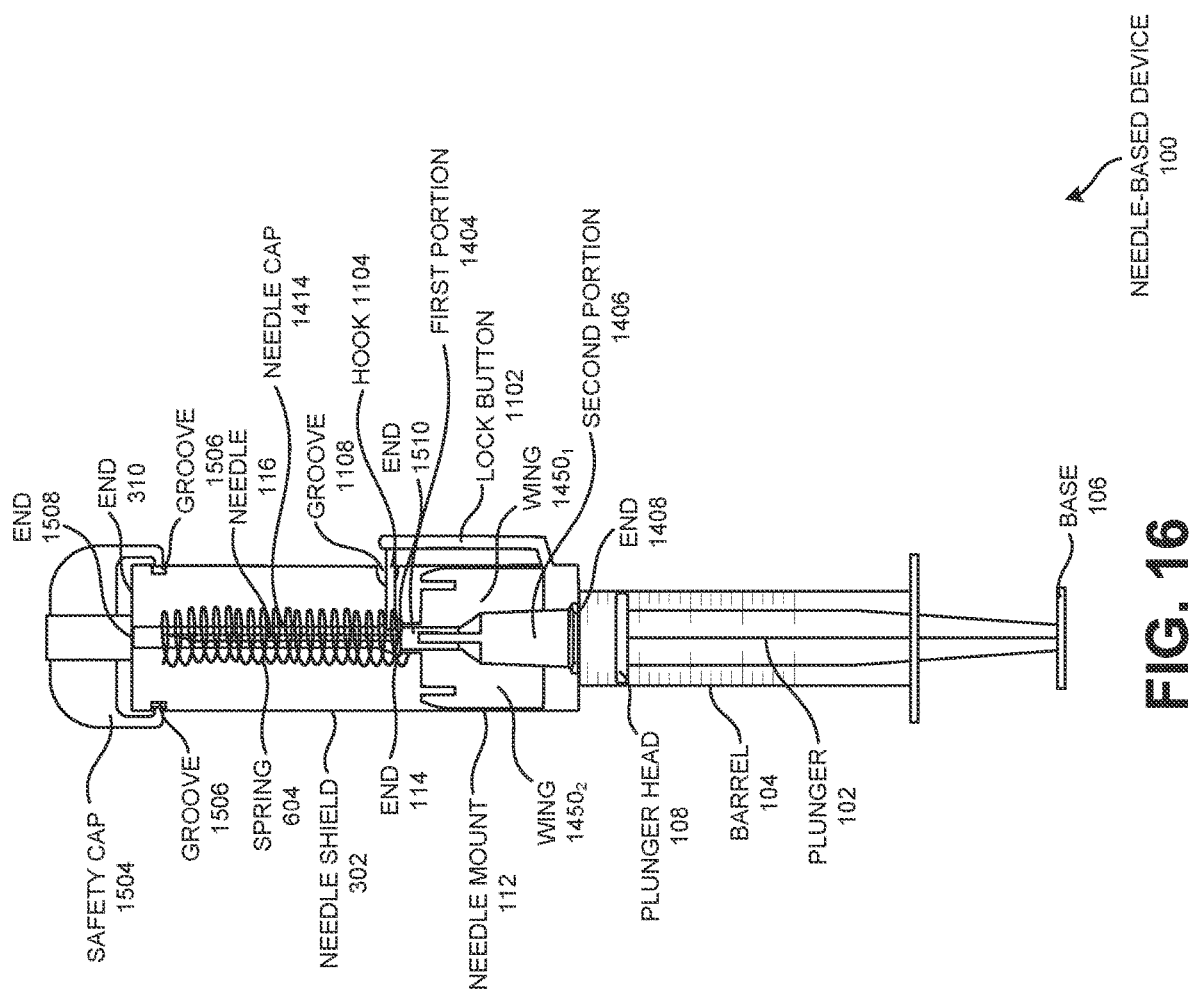
FIG. 16 is a schematic view of another embodiment of the needle-based device of FIG. 15 in the state of disuse thereof.

FIG. 16 shows another embodiment of needle-based device 100 where needle shield 302 completely covers needle 116, needle cap 1414 and spring 604 in the state of disuse of needle-based device 100. In this embodiment, needle cap 1414 may not protrude out of needle-based device 100. For example, a surface of a top portion of needle cap 1414 may be flush with end 310 of needle shield 302 in the state of disuse of needle-based device 100. In one or more embodiments, safety cap 1504 may again couple to needle cap 1414 and cling onto grooves 1506 in the state of disuse of needle-based device 100 to maintain stability of needle 116 therein and to prevent movement of needle 116 out of needle-based device 100.

Figure 17:
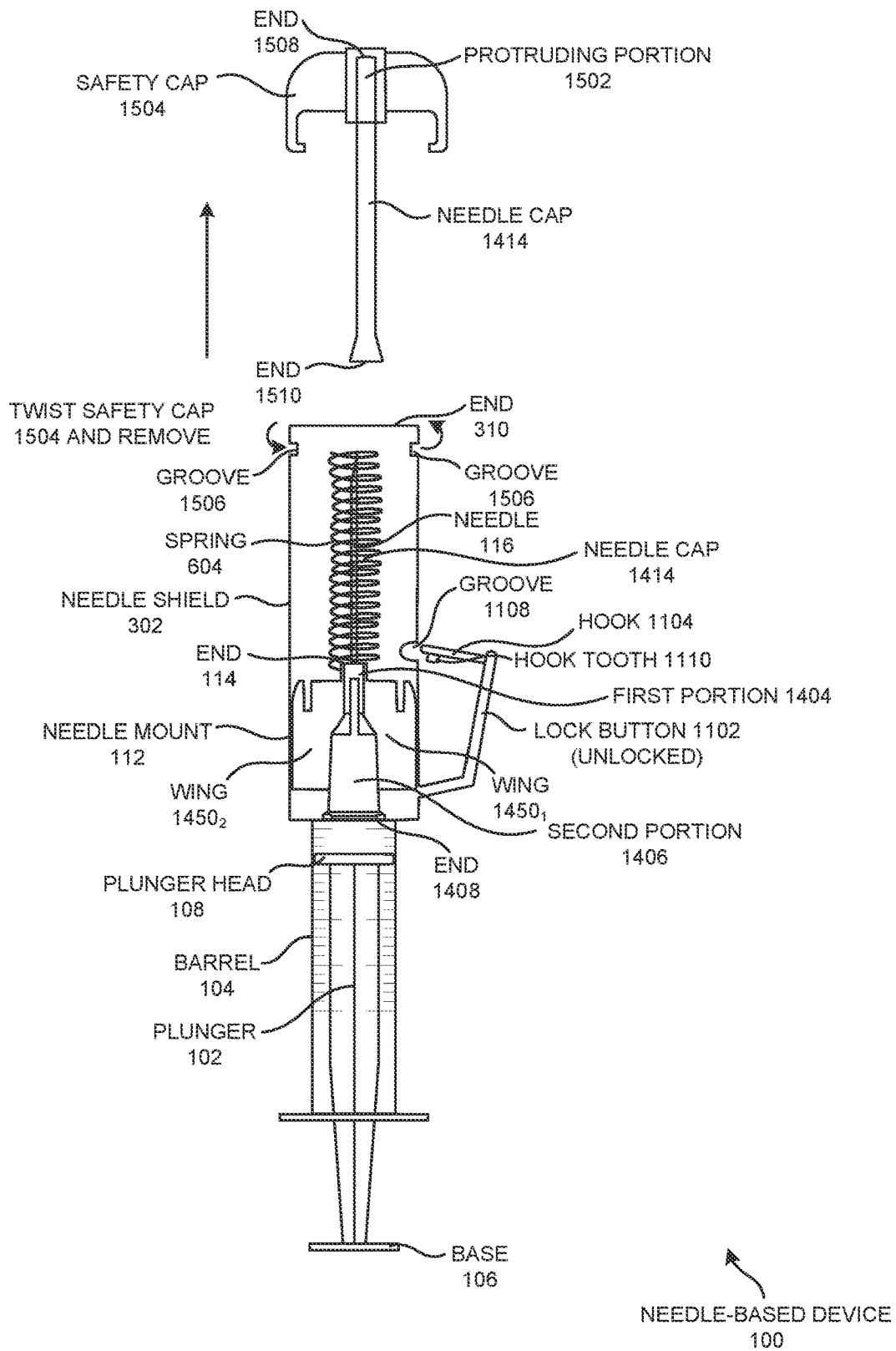
FIG. 17 is a schematic view of a state of enablement of use of the needle-based device in accordance with the embodiments of FIGS. 14-16.

It is obvious that grooves 1506 on the outer wall of needle shield 302 may be holes instead for elements (e.g., wings) of safety cap 1504 to latch onto. All possible means of coupling between safety cap 1504 and needle shield 302 and safety cap 1504 and needle cap 1414 are within the scope of the exemplary embodiments discussed herein. FIG. 17 illustrates the state of enablement of use of needle-based device in accordance with the embodiments of FIGS. 14-16. Here, safety cap 1504 may be removed, for example, by twisting (e.g., by user 150) thereof that disengages safety cap 1504 from grooves 1506 (or, holes) on needle shield 302. The disengagement of safety cap 1504 may render it easy for user 150 to pull safety cap 1504 along with needle cap 1414 out of needle shield 302 to render needle 116 encompassed only by spring 604 and needle shield 302. Also, the aforementioned disengagement process does not dislodge needle 116 out of needle mount 112.

Now the functioning of needle-based device 100 with respect to withdrawing fluid and injecting fluid into user 150 (or, other mammals) is obvious in view of the discussion above relevant to FIGS. 6-7 and FIGS. 9-13. The pressing of needle-based device 100 onto the arm of user 150 may move needle shield 302 downward toward barrel 104, which compresses spring 604. Immediately after the aforementioned force is relaxed or withdrawn, the restoring force of spring 604 may bring back needle shield 302 to an original position thereof that signifies disuse. In other words, the restoring force of spring 604 may decompress spring 604 and restore needle shield 302 back to a state of completely encompassing needle 116 and spring 604 in the state of disuse of needle-based device 100. In this state of disuse, needle 116 may additionally be protected through a lock button (to be discussed below), needle cap 1414 and safety cap 1504.

In the abovementioned embodiments of FIGS. 14-16, needle shield 302 may also include a lock button (e.g., lock button 1102, external lock button 1202) similar to the embodiments of FIGS. 12-13. FIGS. 14-16 show needle-based device 100 as having lock button 1102 merely as an example. In the state of disuse of needle-based device 100, lock button 1102 may catch onto wires of spring 604 through hook 1104 and hook tooth 1110 thereof, which provides additional stability to needle-based device 100. It should be noted that lock button 1102 may also merely lock (e.g., through hook 1104) onto needle shield 302 without catching onto wires of spring 604 in the state of disuse of needle-based device 100.

Figure 18:
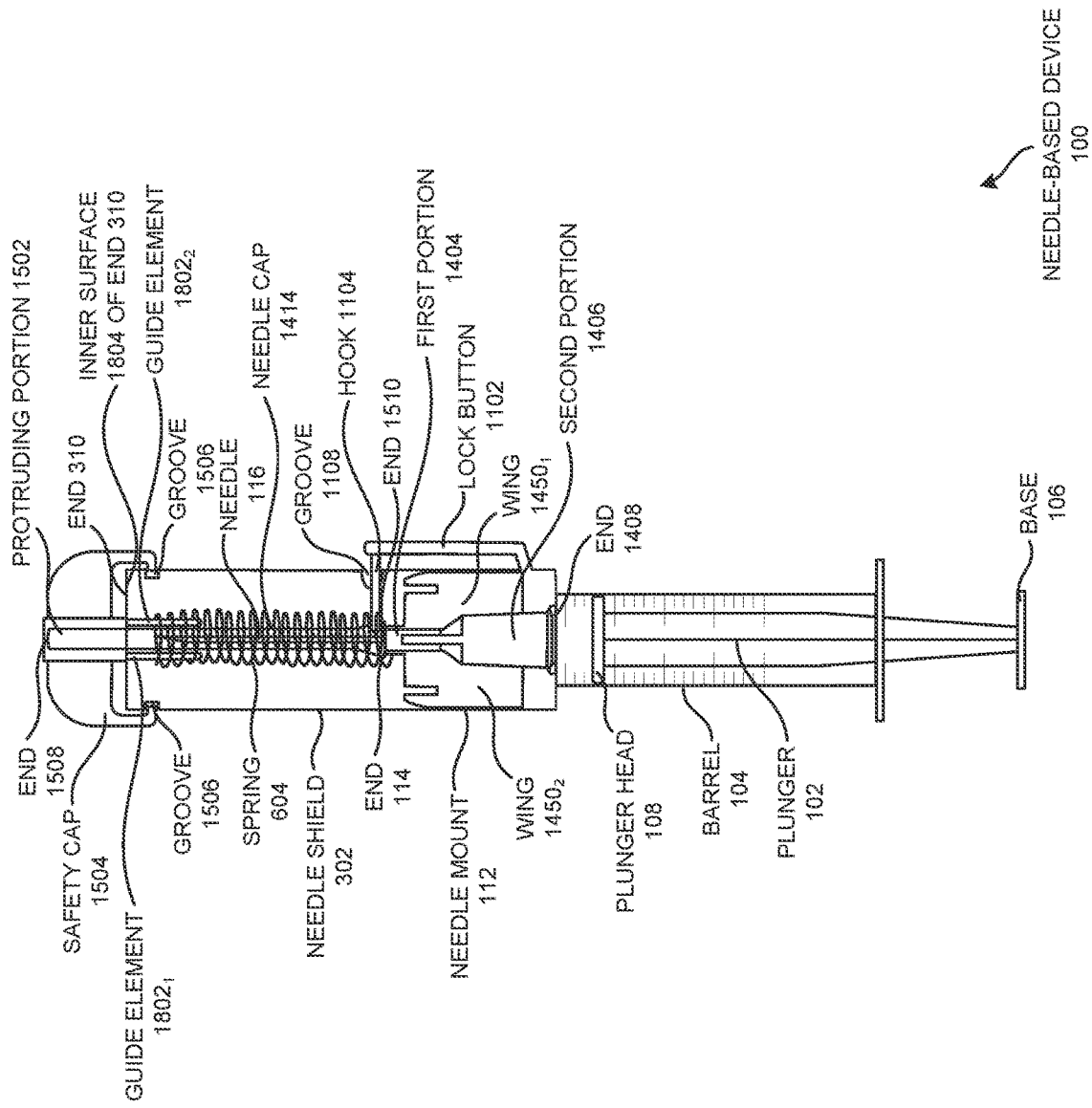
FIG. 18 is a schematic view of the needle-based device of FIG. 15 with guide elements, according to one or more embodiments.

FIG. 18 shows needle-based device 100 in the embodiment of FIG. 15 with guide elements $1802_{1-2}$ on an inner surface thereof proximate end 310. FIG. 18 shows a frontal sliced view of needle shield 302 that illustrates the aforementioned guide elements $1802_{1-2}$ clearly. In one or more embodiments, guide elements $1802_{1-2}$ may be in the form of plates formed on an inner surface/inner wall of end 310 of needle shield 302 of needle-based device 100. In one or more embodiments, the formation of guide elements $1802_{1-2}$ on an inner surface 1804 of end 310 of needle shield 302 may further constrict the space around needle cap 1414 in the state of disuse of needle-based device 100 based on guide elements $1802_{1-2}$ protruding from end 310 inside needle shield 310 parallel to the length of needle shield 302 such that the distance between guide element $1802_1$ and guide element $1802_2$ is less than an inner diameter of needle shield 302. Such a constriction imposed through needle cap 1414 passing through guide elements $1802_{1-2}$ in the state of disuse of needle-based device 100 may prevent significant lateral movement/displacement of needle cap 1414 and, thereby, needle 116 in the state of disuse of needle-based device 100.

The prevention of significant lateral displacement may, in turn, prevent damage to needle 116 and injury to user 150 carrying needle-based device 100 in the state of disuse thereof. Obviously, the length of guide elements $1802_{1-2}$ may be significantly less than the length of needle shield 302 as guide elements $1802_{1-2}$ may internally protrude from end 310 of needle shield 302 to a distance significantly less than the length of needle shield 302. Also, the distance between guide element $1802_1$ and guide element $1802_2$ along a direction perpendicular to the length of needle shield 302 may be less than an inner diameter of needle shield 302. Further, the distance between guide element $1802_1$ and guide element 18022 along the direction perpendicular to the length of needle shield 302 may be less than an inner diameter of spring 604 to enable guide elements $1802_{1-2}$ to pass through spring 604 in the state of disuse of needle-based device 100, as shown in FIG. 18.

It is obvious that the embodiments of FIGS. 14-18 are enhancements of the embodiments discussed with regard to FIGS. 1-13. Therefore, operations/functionalities discussed with regard to FIGS. 1-13 are also applicable to the embodiments of FIGS. 14-18. All reasonable variations are within the scope of the exemplary embodiments discussed herein.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

What is claimed is:

1. A needle-based device comprising:
   a body;
   a needle protruding from the body for a length thereof;
   a needle shield encompassing an entirety of the protruding length of the needle to protect the needle in a first state of disuse of the needle-based device, wherein the needle shield is retracted in a first direction toward the body to apply a first force in the first direction to cause the needle to emerge out of the needle shield to prepare the needle-based device for a second state of use thereof; and a lock button with a first end either integrally formed with the needle shield or external to the needle shield and then coupled to the needle shield, the lock button comprising a hook at a second end thereof, wherein a length of the lock button is completely external to the needle shield, and wherein the needle shield is locked using the lock button in the first state of disuse of the needle-based device in accordance with the hook of the lock button passing through a groove formed on the needle shield and locking directly on to a top of the body from which the needle protrudes such that, in a state of the locking of the needle shield:

the length of the lock button completely external to the needle shield is parallel to a length of the needle shield and the entire protruding length of the needle, and the hook is perpendicular to the length of the needle shield, the length of the lock button and the entire protruding length of the needle.

2. The needle-based device of claim 1, wherein the body comprises one of:

a needle mount coupled to a barrel of the needle-based device, and the barrel of the needle-based device.

3. The needle-based device of claim 2, wherein the barrel is associated with at least one of: a hypodermic syringe, a hypodermic needle, a pen injector and a fluid collection device.

4. The needle-based device of claim 1, wherein the needle-based device is transitioned back to the first state of disuse thereof following the second state of use in accordance with applying a second force in a second direction diametrically opposite to the first direction.

5. The needle-based device of claim 1, wherein lateral sides of the body comprise wings to enable coupling between the needle shield and the body to securely maintain the encompassing of the entire protruding length of the needle by the needle shield in the first state of disuse of the needle-based device.

6. The needle-based device of claim 5, wherein the coupling between the needle shield and the body occurs by way of the wings and one of: a connector and a ring on an outer wall of the body.

7. The needle-based device of claim 1, wherein the second state of use encompasses at least one of: drawing of a fluid and injection of the fluid via the needle-based device.

8. The needle-based device of claim 1, further comprising a needle cap completely encompassing the needle in the first state of disuse of the needle-based device, wherein the needle shield encompasses at least a partial length of the needle cap in addition to the entire protruding length of the needle in the first state of disuse of the needle-based device, and wherein a length of the needle cap protrudes outside the needle shield from an end of the needle shield farthest away from the body in the first state of disuse of the needle- based device.

9. The needle-based device of claim 8, further comprising a safety cap to encompass therewithin an entirety of the length of the needle cap protruding outside the needle shield in the first state of disuse of the needle-based device, wherein the safety cap is secured on to an outer surface of the needle shield proximate the end farthest away from the body such that the needle and the needle cap are completely protected and covered during the first state of disuse of the needle-based device, and wherein the encompassing of the entire length of the needle by the needle shield is maintained in the first state of disuse of the needle-based device even when the safety cap along with the needle cap is removed from the end of the needle shield farthest away from the body.

10. The needle-based device of claim 9, wherein the needle shield comprises guide elements protruding internal to the needle shield from the end thereof farthest away from the body in the first state of disuse of the needle-based device in a direction parallel to the length of the needle shield such that the needle cap passes through the guide elements to prevent significant lateral movement of the needle and the needle cap in the first state of disuse of the needle-based device.

11. The needle-based device of claim 10, wherein a distance between the guide elements along a direction perpendicular to the length of the needle shield is less than an inner diameter of the needle shield, and wherein a length of each of the guide elements along the direction of the length of the needle shield is significantly less than the length of the needle shield.

12. A needle-based device comprising:

a body;

a needle protruding from the body for a length thereof;

a needle shield encompassing an entirety of the protruding length of the needle to protect the needle in a first state of disuse of the needle-based device, wherein the needle shield is retracted in a first direction toward the body to apply a first force in the first direction to cause the needle to emerge out of the needle shield to prepare the needle-based device for a second state of use thereof, and wherein the needle-based device is transitioned back to the first state of disuse thereof following the second state of use in accordance with applying a second force in a second direction diametrically opposite to the first direction; and a lock button with a first end either integrally formed with the needle shield or external to the needle shield and then coupled to the needle shield, the lock button comprising a hook at a second end thereof, wherein a length of the lock button is completely external to the needle shield, and wherein the needle shield is locked using the lock button in the first state of disuse of the needle-based device in accordance with the hook of the lock button passing through a groove formed on the needle shield and locking directly on to a top of the body from which the needle protrudes such that, in a state of the locking of the needle shield:

the length of the lock button completely external to the needle shield is parallel to a length of the needle shield and the entire protruding length of the needle, and the hook is perpendicular to the length of the needle shield, the length of the lock button and the entire protruding length of the needle.

13. The needle-based device of claim 12, wherein lateral sides of the body comprise wings to enable coupling between the needle shield and the body to securely maintain the encompassing of the entire protruding length of the needle by the needle shield in the first state of disuse of the needle-based device.

14. The needle-based device of claim 13, wherein the coupling between the needle shield and the body occurs by way of the wings and one of: a connector and a ring on an outer wall of the body.

15. The needle-based device of claim 12, further comprising a needle cap completely encompassing the needle in the first state of disuse of the needle-based device,
   wherein the needle shield encompasses at least a partial length of the needle cap in addition to the entire length of the needle in the first state of disuse of the needle-based device, and
   wherein a length of the needle cap protrudes outside the needle shield from an end of the needle shield farthest away from the body in the first state of disuse of the needle-based device.

16. The needle-based device of claim 15, further comprising a safety cap to encompass therewithin an entirety of the length of the needle cap protruding outside the needle shield in the first state of disuse of the needle-based device,
   wherein the safety cap is secured on to an outer surface of the needle shield proximate the end farthest away from the body such that the needle and the needle cap are completely protected and covered during the first state of disuse of the needle-based device, and
   wherein the encompassing of the entire length of the needle by the needle shield is maintained in the first state of disuse of the needle-based device even when the safety cap along with the needle cap is removed from the end of the needle shield farthest away from the body.

17. The needle-based device of claim 16, wherein the needle shield comprises guide elements protruding internal to the needle shield from the end thereof farthest away from the body in the first state of disuse of the needle-based device in a direction parallel to the length of the needle shield such that the needle cap passes through the guide elements to prevent significant lateral movement of the needle and the needle cap in the first state of disuse of the needle-based device.

18. The needle-based device of claim 17,
   wherein a distance between the guide elements along a direction perpendicular to the length of the needle shield is less than an inner diameter of the needle shield, and
   wherein a length of each of the guide elements along the direction of the length of the needle shield is significantly less than the length of the needle shield.

19. A needle-based device comprising:
   a body;
   a needle protruding from the body for a length thereof;
   a needle shield encompassing an entirety of the protruding length of the needle to protect the needle in a first state of disuse of the needle-based device,
      wherein the needle shield is retracted in a first direction toward the body to apply a first force in the first direction to cause the needle to emerge out of the needle shield to prepare the needle-based device for a second state of use thereof,
      wherein the needle-based device is transitioned back to the first state of disuse thereof following the second state of use in accordance with applying a second force in a second direction diametrically opposite to the first direction,
      wherein the encompassing of the entire protruding length of the needle by the needle shield is securely maintained in the first state of disuse of the needle-based device through coupling between the needle shield and the body, and
      wherein the second state of use of the needle-based device encompasses at least one of: drawing of a fluid and injection of the fluid via the needle-based device; and
   a lock button with a first end either integrally formed with the needle shield or external to the needle shield and then coupled to the needle shield, the lock button comprising a hook at a second end thereof,
      wherein a length of the lock button is completely external to the needle shield, and
      wherein the needle shield is locked using the lock button in the first state of disuse of the needle-based device in accordance with the hook of the lock button passing through a groove formed on the needle shield and locking directly on to a top of the body from which the needle protrudes such that, in a state of the locking of the needle shield:
         the length of the lock button completely external to the needle shield is parallel to a length of the needle shield and the entire protruding length of the needle, and
         the hook is perpendicular to the length of the needle shield, the length of the lock button and the entire protruding length of the needle.

20. The needle-based device of claim 19, wherein the body comprises one of:
   a needle mount coupled to a barrel of the needle-based device, and
   the barrel of the needle-based device.

* * * * *